(12) United States Patent
De Luca et al.

(10) Patent No.: US 9,273,303 B2
(45) Date of Patent: Mar. 1, 2016

(54) DRIED AND STABILIZED READY-TO-USE COMPOSITION CONTAINING NUCLEIC ACID POLYMERIZATION ENZYMES FOR MOLECULAR BIOLOGY APPLICATIONS

(75) Inventors: Ugo De Luca, Milan (IT); Luigi Roveda, Milan (IT); Maurizio Gramegna, Cigognola (IT)

(73) Assignee: Sentinel CH S.p.A., Milan (IT)

( * ) Notice: Subject to any disclaimer, the term of this patent is extended or adjusted under 35 U.S.C. 154(b) by 0 days.

(21) Appl. No.: 13/318,835

(22) PCT Filed: May 19, 2010

(86) PCT No.: PCT/EP2010/056877
§ 371 (c)(1),
(2), (4) Date: Nov. 4, 2011

(87) PCT Pub. No.: WO2010/133628
PCT Pub. Date: Nov. 25, 2010

(65) Prior Publication Data
US 2012/0064536 A1    Mar. 15, 2012

(30) Foreign Application Priority Data

May 19, 2009 (IT) ............................. MI2009A0877

(51) Int. Cl.
| C12Q 1/68 | (2006.01) |
| C12P 19/34 | (2006.01) |
| C12N 9/96 | (2006.01) |
| C12N 9/12 | (2006.01) |

(52) U.S. Cl.
CPC ............... *C12N 9/96* (2013.01); *C12N 9/1252* (2013.01); *C12Q 1/6844* (2013.01)

(58) Field of Classification Search
None
See application file for complete search history.

(56) References Cited

U.S. PATENT DOCUMENTS

| 4,806,343 A |   | 2/1989 | Carpenter et al. |
| 5,240,843 A | * | 8/1993 | Gibson et al. ................. 435/188 |
| 5,763,157 A | * | 6/1998 | Treml et al. ........................ 435/4 |
| 5,834,254 A |   | 11/1998 | Shen |
| 2004/0072167 A1 | * | 4/2004 | Perry et al. ........................ 435/6 |
| 2004/0182719 A1 |   | 9/2004 | Purvis |

FOREIGN PATENT DOCUMENTS

| CN | 101360822 A | 2/2009 |
| JP | 62-221697 A | 9/1987 |
| JP | 10-503383 A | 3/1998 |
| WO | WO-96/24664 A1 | 8/1996 |
| WO | WO-2007-075253 A2 | 7/2007 |

OTHER PUBLICATIONS

ABI Prism dGTP BigDye Terminator v3.0 Ready Reaction Cycle Sequencing Kit. Applied Biosystems (2002, 2010).*
Redway et al., "Effect of Carbohydrates and Related Compounds on the Long-Term Preservation of Freeze-Dried Bacteria," Cryobiol. 11:73-79, 1974.
International Search Report from International Application No. PCT/EP2010/056877, dated Jul. 7, 2010 (date of completion of search) and Jul. 29, 2010 (date of mailing of report).
Written Opinion from International Application No. PCT/EP2010/056877, dated Jul. 7, 2010 (date of completion of report) and Jul. 29, 2010 (date of mailing of opinion).
International Preliminary Report on Patentability from International Application No. PCT/EP2010/056877, dated May 9, 2011.
Zhu et al., "The development of cryoprotector of biologic products and its protective mechanism," J Kashgar Teachers College. 28(3):46-50 (2007). English language abstract provided.

* cited by examiner

*Primary Examiner* — Young J Kim
(74) *Attorney, Agent, or Firm* — Clark & Elbing LLP; Susan M. Michaud

(57) ABSTRACT

The present invention relates to a exsiccated or lyophilized composition comprising: a nucleic acid polymerization enzyme and cellobiose, in which the enzyme is stable for a period of time, even at a temperature of up to 55° C. The composition of the invention can also comprise further reagents, such as salts, primers specific for a template DNA present in a sample, probes, etc. The invention relates to a method for preparing an exsiccated or lyophilized composition comprising a nucleic acid polymerization enzyme and cellobiose, possibly in containers, in which the enzyme is lyophilized and ready for use in molecular biology applications upon addition of the sample.

15 Claims, 16 Drawing Sheets

FIG. 16
FIG. 16a
Before purification
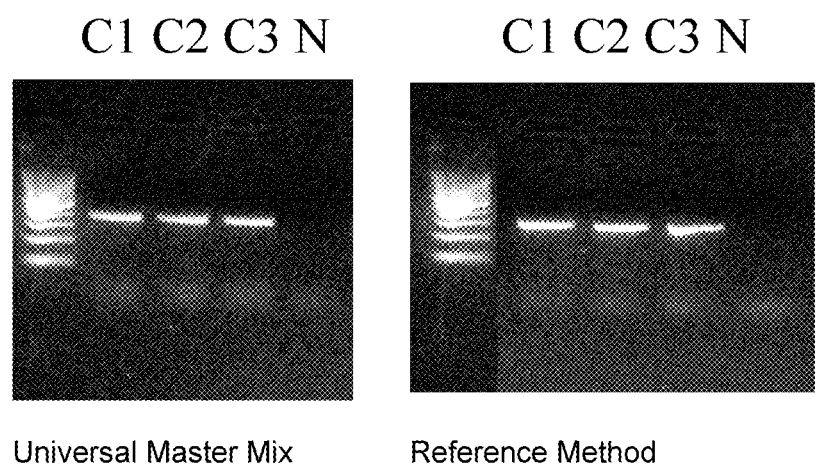
Universal Master Mix          Reference Method
FIG. 16b
After purification
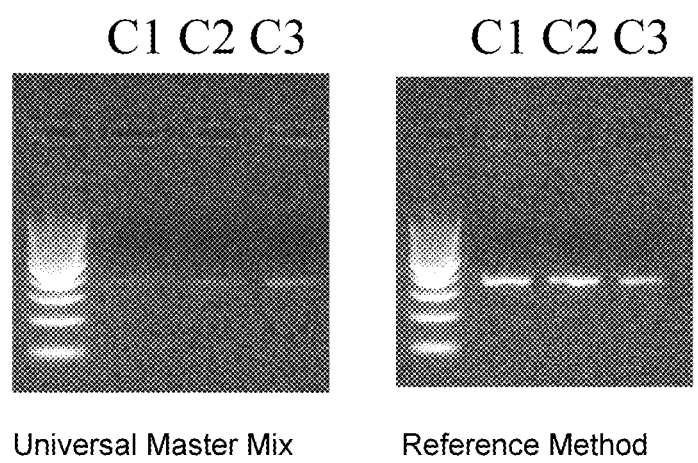
Universal Master Mix          Reference Method FIG. 17
FIG. 17a
Universal Master Mix
wildtype                    mutant (A>G variation)
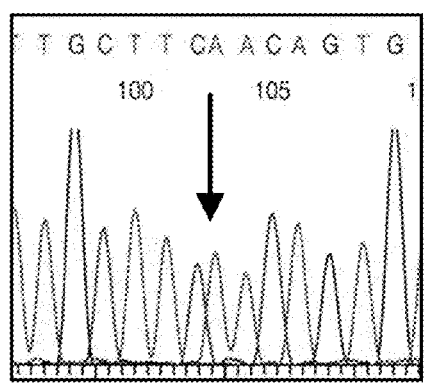     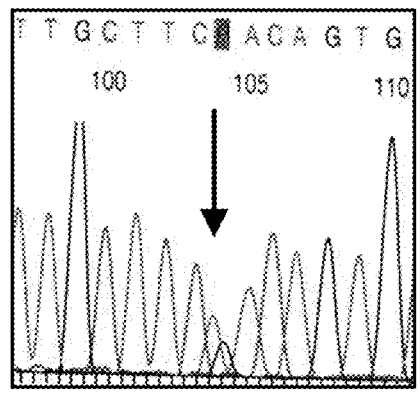
FIG. 17b
Reference Method
wildtype                    mutant (A>G variation)
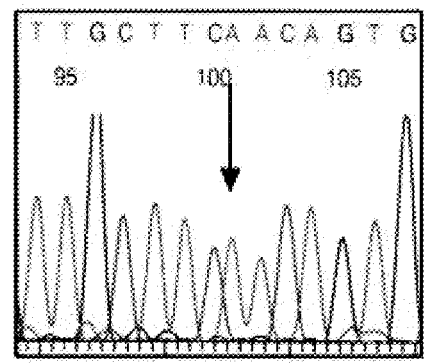     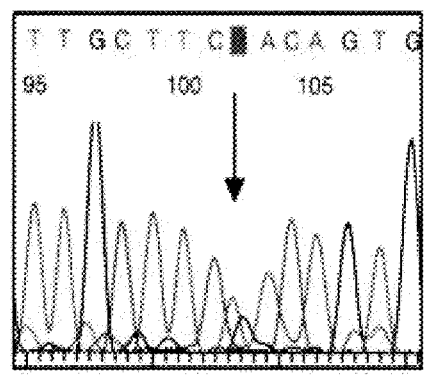

FIG. 18
FIG. 18a
Universal Master Mix
C1 C2 C3
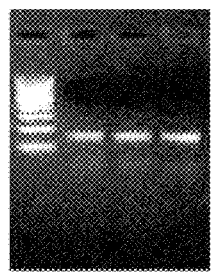
(i)
Cut off curve
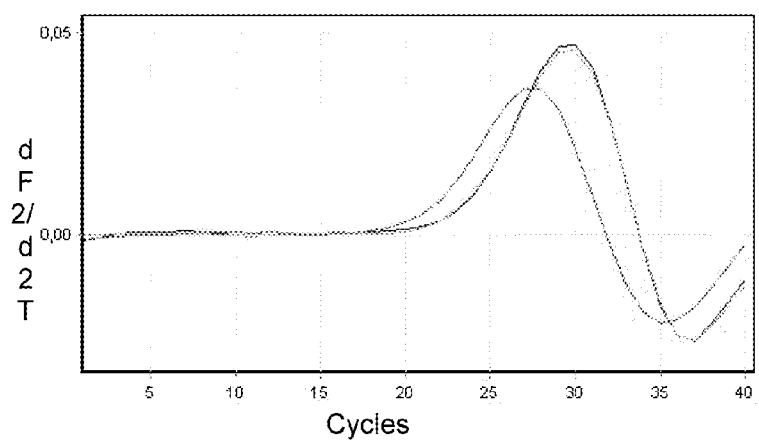
(ii)
| Colour | Name | Take Off | Amplification | Comparative Conc. |
|---|---|---|---|---|
| ■ | C1 | 24,6 | 1,58 | 7,26E-06 |
| ░ | C2 | 24,5 | 1,57 | 7,62E-06 |
| ▓ | C3 | 22,3 | 1,70 | 2,20E-05 |
(iii)

Reference Method

C1 C2 C3

(i)

Cut off curve (ii)

| No. | Colour | Name | Take Off | Efficiency | Comparative Conc. |
|---|---|---|---|---|---|
| 5 | | C1 | 24,5 | 1,63 | 1,00E+00 |
| 6 | | C2 | 22,6 | 1,79 | 2,91E+00 |
| 7 | | C3 | 24,1 | 1,84 | 1,25E+00 |

(iii)

FIG. 19
FIG. 19a
Universal Master Mix
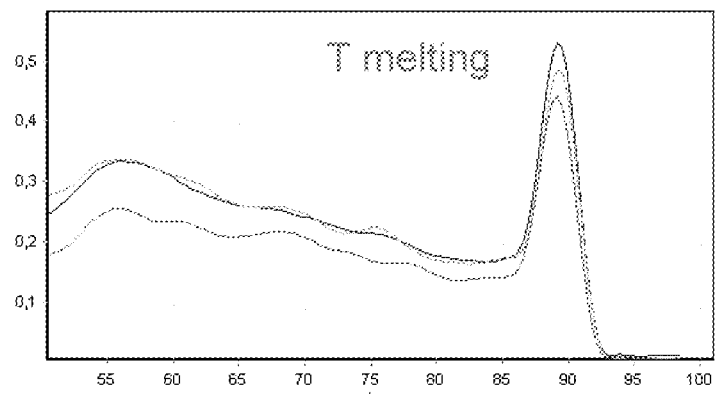
FIG. 19b
Reference Method
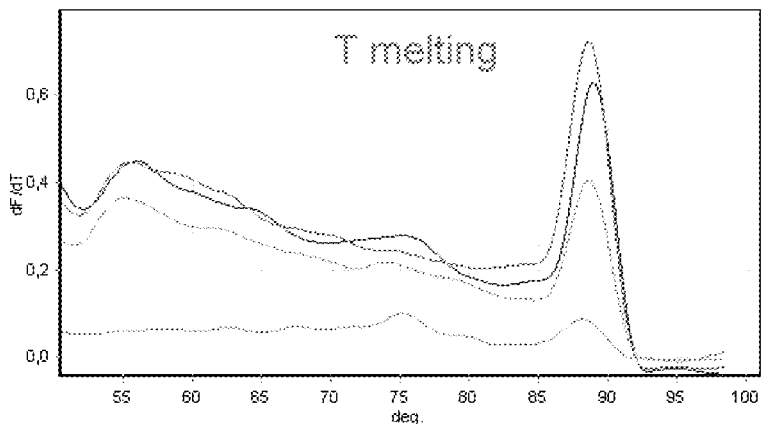

FIG. 20
FIG. 20a
Universal Master Mix
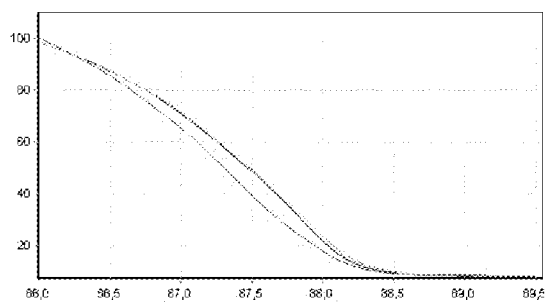
Range 85°C – 96°C
FIG. 20b
Reference Method
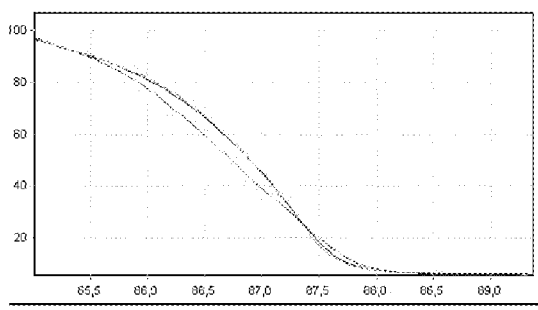
Range 85°C – 96°C FIG. 21a: Universal Master Mix

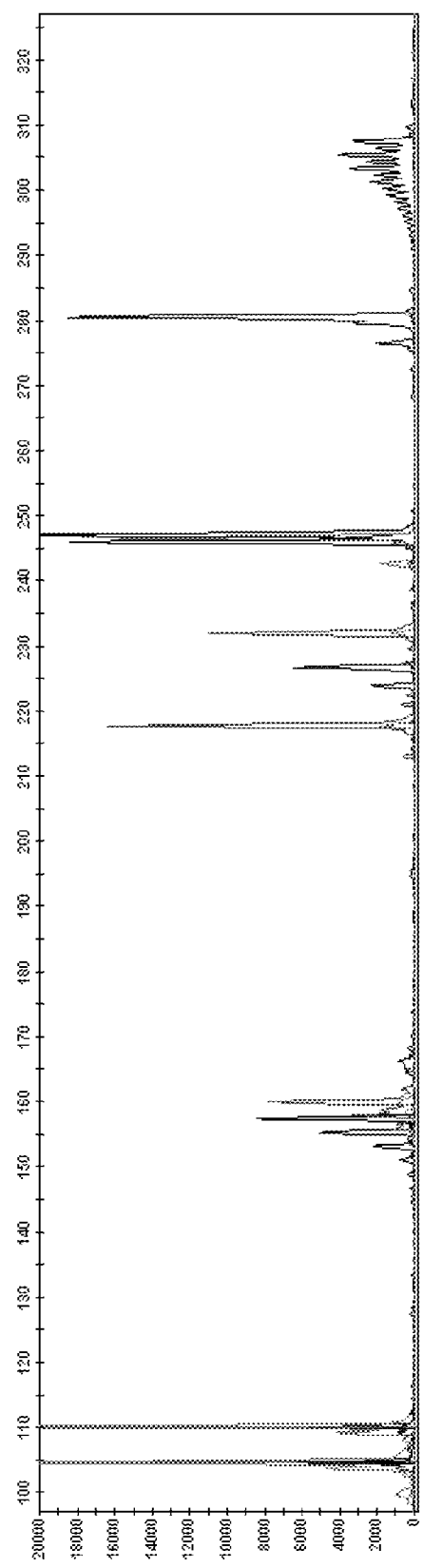
FIG. 21b: Reference Method

DRIED AND STABILIZED READY-TO-USE COMPOSITION CONTAINING NUCLEIC ACID POLYMERIZATION ENZYMES FOR MOLECULAR BIOLOGY APPLICATIONS

CROSS-REFERENCE TO RELATED APPLICATIONS

This application is the U.S. national stage filing under 35 U.S.C. §371 of international application PCT/EP2010/056877, filed May 19, 2010, which claims benefit of Italian Patent Application MI2009A000877, filed May 19, 2009.

FIELD OF THE INVENTION

The present invention relates to the stabilization of nucleic acid polymerase enzymes and to the preparation of ready-to-use reaction compositions and kits containing such a polymerase stabilizer, usable also for diagnostic purposes.

PRIOR ART

The in vivo and in vitro synthesis of nucleic acids is controlled by the exact replication of the strands, where each single nucleic acid strand determines the order of nucleotides in a perfectly complementary strand. The specific mechanism for DNA replication entails the use, and is carried out by, an enzyme family known as polymerases.

Polymerases, purified from various organisms, are commonly used in research and diagnostics, in particular with the advent of various systems of gene amplification such as the Polymerase Chain Reaction (PCR—Mullis et al. U.S. Pat. Nos. 4,683,195; 4,683,202; and 4,800,159).

The basic configuration of PCR consists of two synthesized primers, a nucleic acid template and the polymerase enzyme. Each primer is complementary to a region in the target nucleic acid, or better still, to one of the two complementary strands.

The polymerase enzyme is obviously a critical part of the amplification system on account of its capacity to add nucleotides sequentially in a 3' direction, binding them to a hydroxyl group of the target-specific polynucleotide primer which is able to bind to the template strand through hydrogen bonds.

A standard amplification mixture can have the following composition: dNTPs, a buffer, $MgCl_2$, a forward primer, a reverse primer, Taq polymerase, DNA and $H_2O$. The reaction mixture must be heated to 90-95° C. to denature the double helix of the template DNA. After the denaturation step the temperature is reduced to 50-60° C. to allow annealing of the primers to the complementary strand; the polymerase completes the process by elongating said primers in a step commonly known as extension.

The enzymes used in PCR reactions have been isolated from thermophilic organisms and are therefore stable at high temperatures. Nevertheless, even these highly heat-stable enzymes can be inactivated by chemical agents, proteases, or environmental changes.

The use of heat-stable enzymes, as with other enzymes, often requires the concomitant use of denaturation conditions such as high temperatures, as is the case with PCR, aqueous mixtures with sub-optimal concentrations of co-factors and substrates, and a non-optimal pH for maximum enzyme activity.

This scenario suggests that stabilization of the enzymes is strongly desired and necessary for a long term preservation of the enzymes, especially if included in aqueous mixtures together with other reagents and ready-to-use reaction mixtures for amplifying nucleic acids.

A number of techniques for stabilizing polymerases are known and have been described in patents and applications. Said techniques include chemical modification of the enzymes, immobilization on solid supports, use of aptamers, genetic engineering of the enzymes and addition of stabilizing agents.

A group of substances that has demonstrated a stabilizing activity are surfactants which function at the interface between the active form of the enzyme and the aqueous environment in which they are contained.

The usual method of stabilizing the enzymes used in molecular biology techniques is by storing a liquid preparation of each enzyme in a solution containing 50% glycerol and a reducing agent such as dithiothreitol (DTT) or β-mercaptoethanol at −20° C. The procedure is sufficient to preserve the activity of the enzymes for many months with minimal loss of activity. In contrast, enzyme activity is rapidly lost when stored at room temperature or at +4° C.

Non-ionic detergents such as Triton X-100 and Tween 20 have been shown to stabilize DNA polymerase activity. Patent application EP 776,970 A1 describes the use of non-ionic detergents, including Tween20® and NP-40® to stabilize the activity of heat-stable DNA polymerases. Sodium dodecyl sulphate (SDS) at low concentrations has also been shown to stabilize enzyme activity.

Methods for preserving enzymes which enable them to tolerate prolonged exposure to room temperature or brief exposure to higher temperatures, are still the only real limitation to an easier and more cost effective management of postal consignments and utilization in new fields. Enzymes, and particularly polymerases including those derived from thermophilic organisms i.e. those normally utilized for polymerase chain reactions (PCR), have hitherto been transported at temperatures lower than +2-8° C., and normally at −20° C.

Of the methods for preserving biological materials, lyophilization has hitherto been used for preserving foods, cells, biological membranes, biological macromolecules and even enzymes.

The lyophilization process involves the removal of water from a frozen sample, i.e. the evaporation of the aqueous component of the solid without passing through the liquid state, under lower than room pressure conditions.

The protein preparations are normally frozen before being exsiccated to reduce structural distortions due to the exsiccation.

An incompletely dried lyophilization i.e. one that still contains a low percentage of water, seems to ensure a better preservation than a completely exsiccated one, particularly if followed by preservation at a temperature no higher than +4-10° C. Even under these conditions, however, there is a small loss of enzyme activity.

Some enzymes such as polymerases, however, are completely inactivated after lyophilization in the absence of a cryoprotectant, regardless of the type of lyophilization (dry or otherwise).

A number of substances or additives with cryoprotective activity have been used or proposed for stabilizing polymerases. For example, U.S. Pat. Nos. 5,614,387 and 5,834,254 describe methods and compositions for preparing stable lyophilized enzyme compositions for amplifying nucleic acids in which trehalose and/or polyvinyl pyrrolidone (PVP) were used as cryoprotective agents.

Analysis of the known art and products currently on the market shows that the problem of preserving polymerization enzymes and the potential for simplifying the preparation of polymerization chain reaction mixtures (and hence standardization of PCR reactions even in the laboratory environment) are extremely topical and in continuous development.

Available on the market is a system known as puRe Taq Ready-To-Go PCR Beads (GE Healthcare) consisting of a pre-mixed lyophilized formulation in single dose for standard PCR amplifications. However, the system has the limitation of being prepared with a specific Taq polymerase (puRe Taq polymerase) described as the leading enzyme for its stability and purity. By contrast, the proposed method of the present invention can be used with all polymerases because cellobiose is able to stabilize and protect all Taq polymerases, whether simple polymerases or Hot Start polymerases or even their active fragments such as Klenow.

SUMMARY

The present invention relates to an exsiccated or lyophilized composition suitable for being diluted with an appropriate solvent, comprising a nucleic acid polymerization enzyme stabilized to withstand lyophilisation and storage at a temperature of up to 55° C., characterized in that said composition has a nucleic acid polymerization enzyme concentration in the range from 0.01 to 250 Units (0, 4-10000 U/ml), cellobiose in a concentration in the range from 50 mM (17.115 g/L) to 500 mM (171.15 g/L) and a buffer. Said nucleic acid polymerization enzyme is a DNA polymerase preferably selected from the group consisting of Taq Polymerase, Hot Start polymerase or their active fragments. Said composition is also referred to as a "lyophilized and ready-to-use amplification mixture" or "Universal Master Mix".

A further aspect of the present invention regards a composition suitable for being diluted with an appropriate solvent, comprising a nucleic acid polymerization enzyme stabilized to withstand lyophilisation and storage at a temperature up to 55° C., characterized in that said composition has a nucleic acid polymerization enzyme concentration in the range from 0.01 to 250 Units, cellobiose in a concentration in the range from 50 to 500 mM, a buffer, dNTPs, KCl and $MgCl_2$.

The invention further relates to the use of the composition for the amplification of nucleic acids, in particular for molecular biology applications such as, but not limited to PCR, Real Time PCR, Melting curve analysis, High Resolution Melting analysis, Sequencing, Quantitative Fluorescent PCR, Multiplex PCR, Whole Genome Amplification, Isothermal amplification.

The invention still further relates to a process for the amplification of nucleic acids comprising the steps of:
  i. reconstituting the composition of the invention in water or in a buffer;
  ii. adding primers specific for a target DNA;
  iii. adding a nucleic acid template;
  iv. optionally adding one or more of the reagents selected from the group consisting of: KCl, $MgCl_2$, dNTPs, at least one optionally labelled probe, reducing agents and further stabilizers.

The invention also provides a ready to use product comprising the exsiccated or lyophilized composition according to the invention and a solvent for reconstituting said composition.

Furthermore, the invention comprises kits for PCR amplification of a DNA sample comprising the composition according to the invention and optionally instructions for the reconstitution and use of the enzyme in a polymerase chain reaction.

A particularly preferred embodiment of the invention consists of the use of cellobiose for the preservation of a nucleic acid polymerase during lyophilization and long term storage at a temperature up to 55° C.

M: molecular weight marker "BenchTop PCR Markers", Promega.

PCR products: 268 bp: fragment of the human beta-globin gene; 240 bp; fragment of the *Plasmodium* spp 18s RNA gene.

Figure 2:
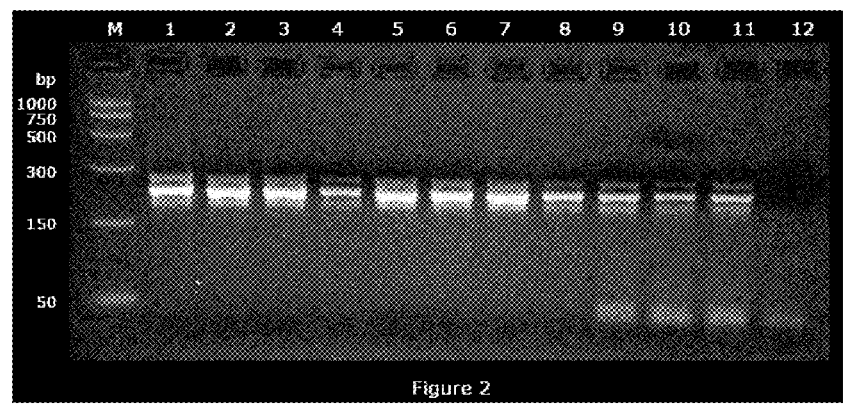

FIG. 2. Agarose gel electrophoretic pattern of lyophilized and ready-to-use amplification mixtures, after preservation at room temperature or at 37° C. for three weeks. Lanes 1-8: amplification products obtained with the amplification mixtures containing Hot Start DNA polymerases of company X; volume before lyophilization: 25 µl (lanes 1-4) or 9.1 µl (lanes 5-8). Lanes 9-12: amplification products obtained with lyophilized and ready-to-use reaction mixtures containing DNA polymerase of company X; volume before lyophilization: 25 µl. Preservation for three weeks at room temperature (lanes 1-3, 5-7, 9-11) or at 37° C. (lanes 4, 8, 12).

M: molecular weight marker "BenchTop PCR Markers", Promega.

PCR products: 268 bp: fragment of the human beta-globin gene; 240 bp; fragment of the *Plasmodium* spp 18s RNA gene.

Figure 3:
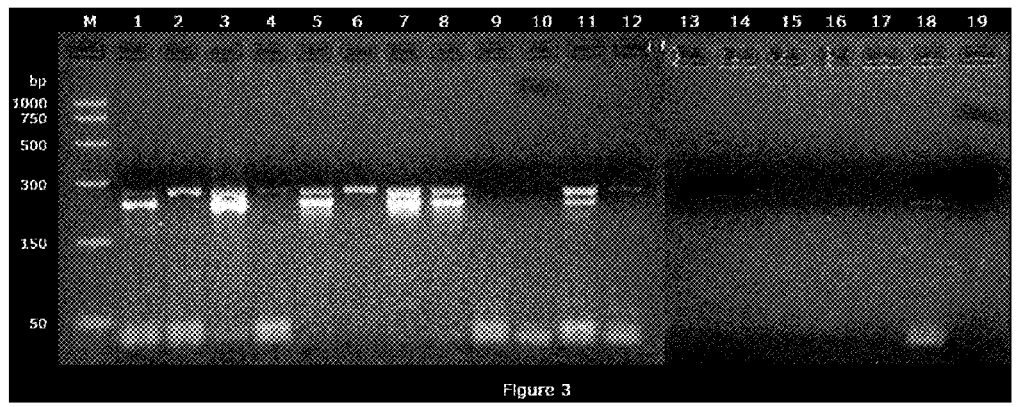

FIG. 3. Agarose gel electrophoretic pattern of lyophilized and ready-to-use amplification mixtures, immediately following completion of the lyophilization process. The lyophilized and ready-to-use mixtures contain: (i) reaction buffers of company W (lanes 1-4), of company X (lanes 5-8), of company R (lanes 9-12) or company Y (lanes 13-19); (ii) Hot Start DNA polymerases obtained from company W (lanes 1, 5, 9 and 13), from company Y (lanes 2, 6, 10, 14, 17, 18 and 19), from company X (lanes 3, 7, 11 and 15) or from company R (lanes 4, 8, 12 and 16). The amplification products of lanes 17, 18 and 19 were obtained with lyophilized and ready-to-use mixtures also containing, respectively, 0.25% NP-40 and 0.25% Tween-20, 100 mM sucrose and 0.25% NP-40, 0.25% Tween-20 and 100 mM sucrose.

M: molecular weight marker "BenchTop PCR Markers", Promega.

PCR products: 268 bp: fragment of the human beta-globin gene; 240 bp; fragment of the *Plasmodium* spp 18s RNA gene.

Figure 4:
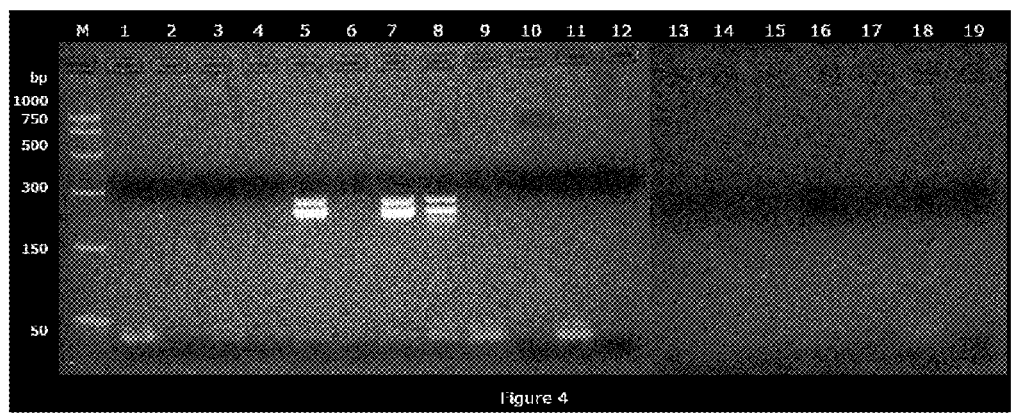

FIG. 4. Agarose gel electrophoretic pattern of lyophilized and ready-to-use amplification mixtures, after preservation at room temperature for six weeks. The lyophilized and ready-to-use mixtures contain respectively: (i) reaction buffers of company W (lanes 1-4), of company X (lanes 5-8), of company R (lanes 9-12) or of company Y (lanes 13-19); (ii) Hot Start DNA polymerases obtained from company W (lanes 1, 5, 9 and 13), from company Y (lanes 2, 6, 10, 14, 17, 18 and 19), from company X (lanes 3, 7, 11 and 15) or from company R (lanes 4, 8, 12 and 16). The amplification products of lanes 17, 18 and 19 were obtained with lyophilized and ready-to-use mixtures containing also, respectively 0.25% NP-40 and 0.25% Tween-20, 100 mM sucrose and 0.25% NP-40, 0.25% Tween-20 and 100 mM sucrose.

M: molecular weight marker "BenchTop PCR Markers", Promega.

PCR products: 268 bp: fragment of the human beta-globin gene; 240 bp; fragment of the *Plasmodium* spp 18s RNA gene.

Figure 5:
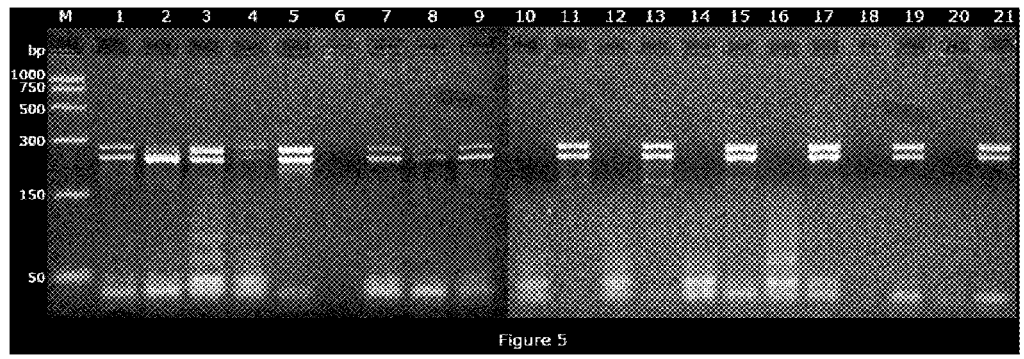

FIG. 5. Agarose gel electrophoretic pattern of lyophilized and ready-to-use amplification mixtures containing 250 mM sucrose, immediately following completion of the lyophilization process. The lyophilized and ready-to-use mixtures contain: (i) reaction buffers of company X (lanes 1, 8 and 9), of company W (lanes 2, 3, 14-17), of company R (lanes 4, 5, 10-13) or of company Y (lanes 6, 7, 18-21); (ii) Hot Start DNA polymerases obtained from company X (lanes 1-7) or from company R (lanes 8-21). In the lyophilized and ready-to-use mixtures used in lanes 1, 2, 4, 6, 8, 10, 14 and 18, no substances were added; in those of lanes 3, 5, 7, 11, 15 and 19, 250 mM sucrose was added to the reaction buffer; in those of lanes 9, 12, 16 and 20, 250 mM sucrose was added to the storage buffer, while in those of lanes 13, 17 and 21, 250 mM sucrose was added both to the reaction buffer and the storage buffer.

M: molecular weight marker "BenchTop PCR Markers", Promega.

PCR products: 268 bp: fragment of the human beta-globin gene; 240 bp; fragment of the *Plasmodium* spp 18s RNA gene.

Figure 6:
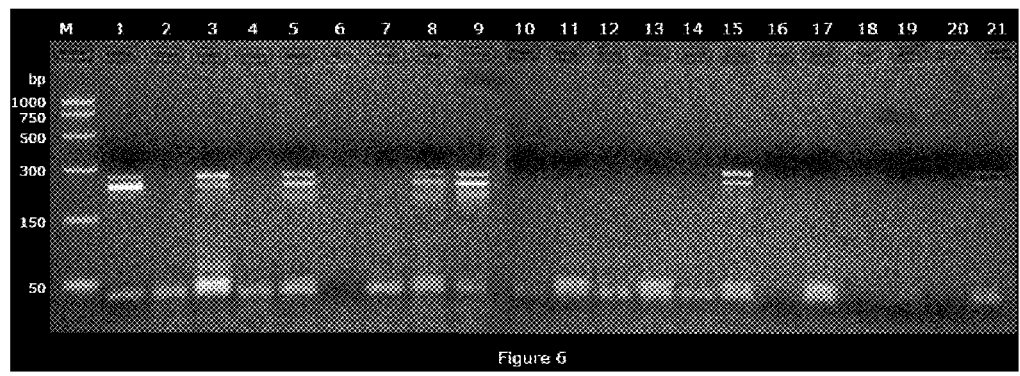

FIG. 6. Agarose gel electrophoretic pattern of lyophilized and ready-to-use amplification mixtures containing 250 mM sucrose, after preservation at room temperature for eight weeks.

The lyophilized and ready-to-use mixtures contain: (i) reaction buffers of company X (lanes 1, 8 and 9), of company W (lanes 2, 3, 14-17), of company R (lanes 4, 5, 10-13) or of company Y (lanes 6, 7, 18-21); (ii) Hot Start DNA polymerases obtained from company X (lanes 1-7) or from company R (lanes 8-21). In the lyophilized and ready-to-use mixtures used in lanes 1, 2, 4, 6, 8, 10, 14 and 18, no substances were added; in those of lanes 3, 5, 7, 11, 15 and 19, 250 mM sucrose was added to the reaction buffer; in those of lanes 9, 12, 16 and 20, 250 mM sucrose was added to the storage buffer, while in those of lanes 13, 17 and 21, 250 mM sucrose was added to both the reaction and storage buffers.

M: molecular weight marker "BenchTop PCR Markers", Promega.

PCR products: 268 bp: fragment of the human beta-globin gene; 240 bp; fragment of the *Plasmodium* spp 18s RNA gene.

Figure 7:
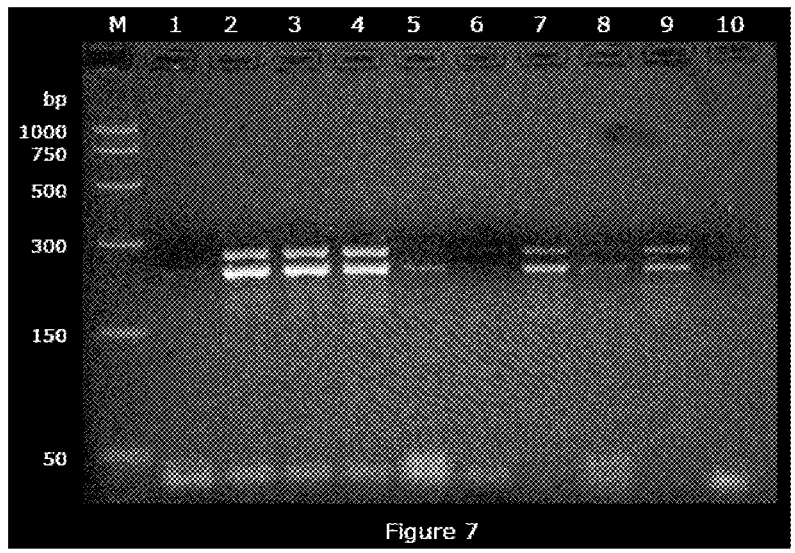

FIG. 7. Agarose gel electrophoretic pattern of lyophilized and ready-to-use amplification mixtures, containing the stabilizers described below, after completion of the lyophilization process. The lyophilized and ready-to-use mixtures contain reaction buffers and the Hot Start DNA polymerase enzymes obtained from company W (lanes 1-5) or from company R (lanes 6-10). Added to the lyophilized and ready-to-use mixtures as the stabilizer was: 200 mM trehalose (lanes 2 and 7), 250 mM sucrose (lanes 3 and 8), 200 mM maltose (lanes 4 and 9) or 0.025% agarose (5 and 10). No substances were added to the lyophilized and ready-to-use mixtures used in lanes 1 and 6.

M: molecular weight marker "BenchTop PCR Markers", Promega.

PCR products: 268 bp: fragment of the human beta-globin gene; 240 bp; fragment of the *Plasmodium* spp 18s RNA gene.

Figure 8:
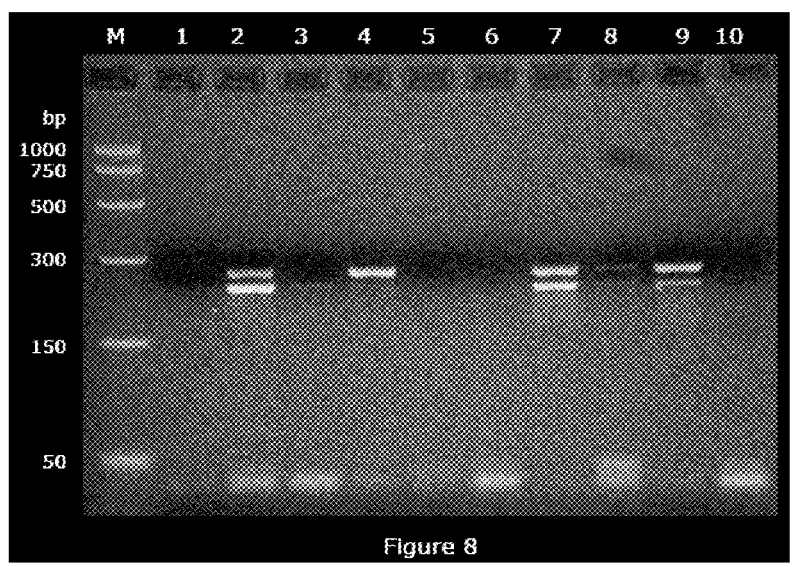

FIG. 8. Agarose gel electrophoretic pattern of lyophilized and ready-to-use amplification mixtures, after preservation at room temperature or at 37° C. for one week. The lyophilized and ready-to-use mixtures contain reaction buffers and the Hot Start DNA polymerase enzymes obtained from company W (lanes 1-5) or from company R (lanes 6-10). Added to the lyophilized and ready-to-use mixtures as the stabilizer was: 200 mM trehalose (lanes 2 and 7), 250 mM sucrose (lanes 3 and 8), 200 mM maltose (lanes 4 and 9) or 0.025% agarose (5 and 10). No substances were added to the lyophilized and ready-to-use mixtures used in lanes 1 and 6.

M: molecular weight marker "BenchTop PCR Markers", Promega.

PCR products: 268 bp: fragment of the human beta-globin gene; 240 bp; fragment of the *Plasmodium* spp 18s RNA gene.

Figure 9:
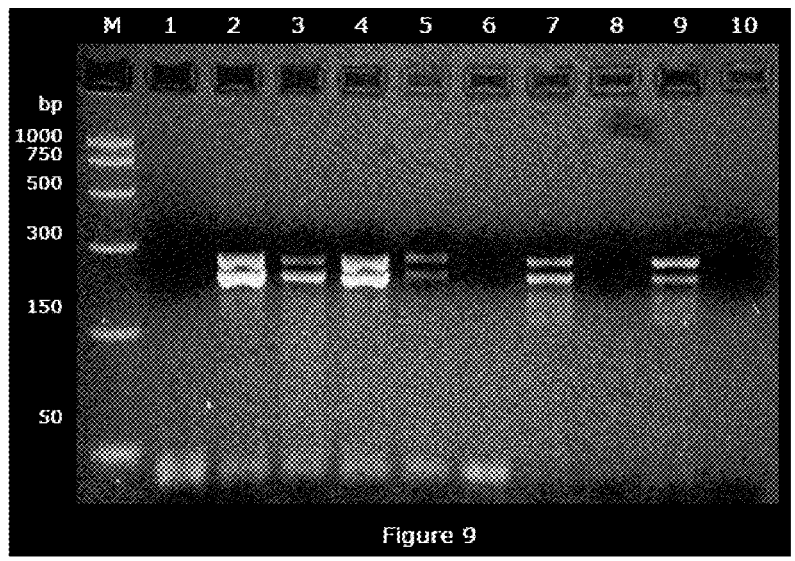

FIG. 9. Agarose gel electrophoretic pattern of lyophilized and ready-to-use amplification mixtures, containing stabilizers, immediately after completion of the lyophilization process. The lyophilized and ready-to-use mixtures contain reaction buffers and Hot Start DNA polymerases obtained from company W (lanes 1-5) or from company R (lanes 6-10). Added to the lyophilized and ready-to-use mixtures was: 250 mM trehalose (lanes 2 and 7), 6.6% dextrose (lanes 3 and 8), 200 mM cellobiose (lanes 4 and 9) or 6.6% amylopectin (5 and 10). No substances were added to the lyophilized and ready-to-use mixtures used in lanes 1 and 6.

M: molecular weight marker "BenchTop PCR Markers", Promega.

PCR products: 268 bp: fragment of the human beta-globin gene; 240 bp; fragment of the *Plasmodium* spp 18s RNA gene.

Figure 10:
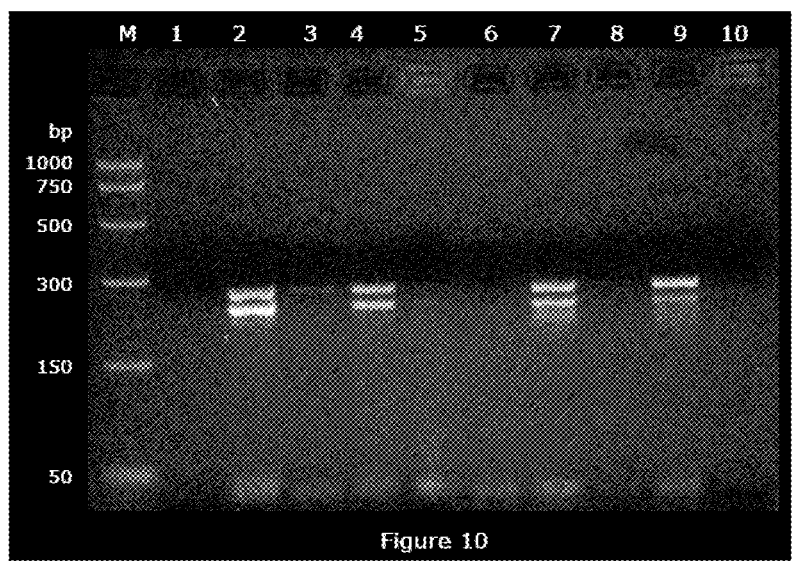

FIG. 10. Agarose gel electrophoretic pattern of lyophilized and ready-to-use amplification mixtures, containing stabilizers, after preservation at 37° C. for one week. The lyophilized and ready-to-use mixtures contain reaction buffers and Hot Start DNA polymerases obtained from company W (lanes 1-5) or from company R (lanes 6-10). Added to the lyophilized and ready-to-use mixtures was: 250 mM trehalose (lanes 2 and 7), 6.6% dextrose (lanes 3 and 8), 200 mM cellobiose (lanes 4 and 9) or 6.6% amylopectin (5 and 10). No substances were added to the lyophilized and ready-to-use mixtures used in lanes 1 and 6.

M: molecular weight marker "BenchTop PCR Markers", Promega.

PCR products: 268 bp: fragment of the human beta-globin gene; 240 bp; fragment of the *Plasmodium* spp 18s RNA gene.

Figure 11:
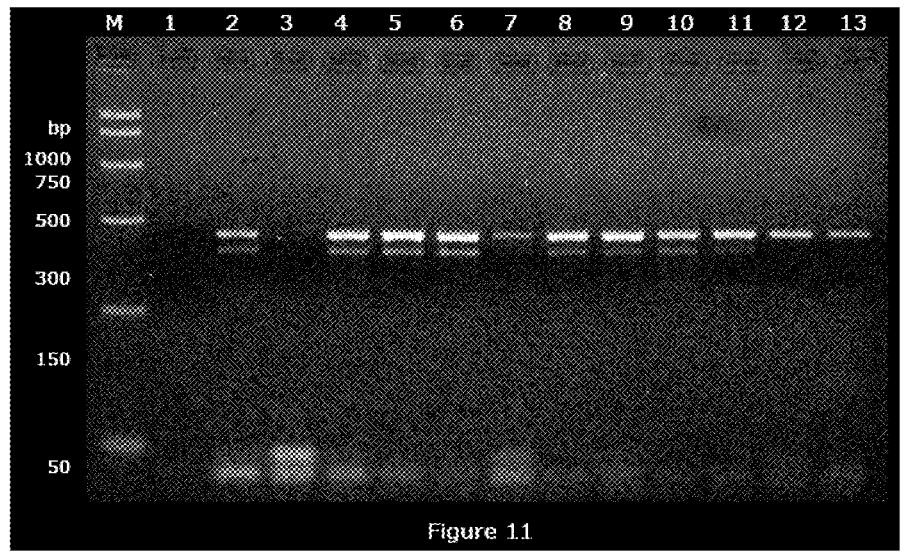

FIG. 11. Agarose gel electrophoretic pattern of lyophilized and ready-to-use amplification mixtures, containing cellobiose, immediately after completion of the lyophilization process. The lyophilized and ready-to-use mixtures contain reaction buffers and Hot Start DNA polymerases obtained from company W (lanes 1-5) or from company R (lanes 6-10). Added to the lyophilized and ready-to-use mixtures was: 250 mM trehalose (lanes 2 and 7), 6.6% dextrose (lanes 3 and 8), 200 mM cellobiose (lanes 4 and 9) or 6.6% amylopectin (5 and 10). No substances were added to the lyophilized and ready-to-use mixtures used in lanes 1 and 6.

M: molecular weight marker "BenchTop PCR Markers", Promega.

PCR products: 268 bp: fragment of the human beta-globin gene; 240 bp; fragment of the *Plasmodium* spp 18s RNA gene.

Figure 12:
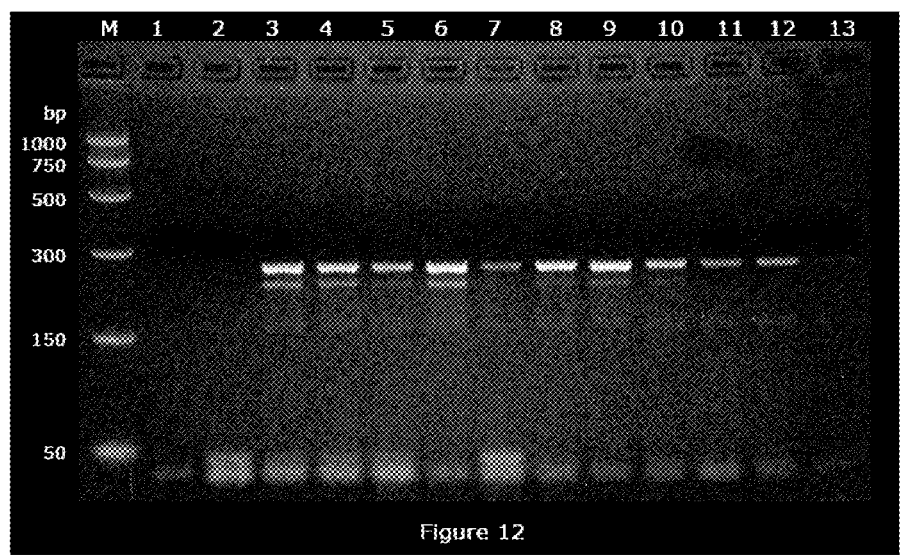

FIG. 12. Agarose gel electrophoretic pattern of lyophilized and ready-to-use amplification mixtures, containing cellobiose, after preservation at 37° C. for two weeks. The lyophilized and ready-to-use mixtures contain reaction buffers and Hot Start DNA polymerases obtained from company R (lanes 1-13). Cellobiose was added at different concentrations (mM) to the lyophilized and ready-to-use mixtures: 0 (lane 1), 50 (lane 2), 100 (lane 3), 150 (lane 4), 200 (lane 5), 250 (lane 6), 300 (lane 7), 350 (lane 8), 400 (lane 9), 450 (lane 10), 500 (lane 11), 600 (lane 12), 700 (lane 13).

M: molecular weight marker "BenchTop PCR Markers", Promega.

PCR products: 268 bp: fragment of the human beta-globin gene; 240 bp; fragment of the *Plasmodium* spp 18s RNA gene.

Figure 13:
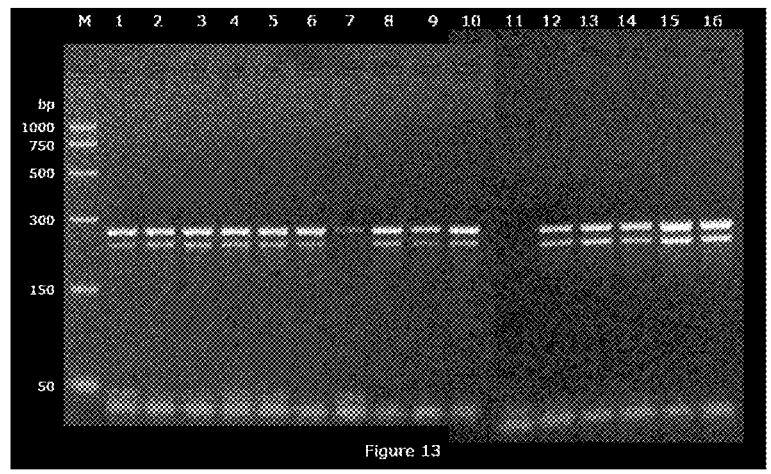

FIG. 13. Agarose gel electrophoretic pattern of lyophilized and ready-to-use to amplification mixtures, containing cellobiose or trehalose, immediately after completion of the lyophilization process. The lyophilized and ready-to-use mixtures contain reaction buffers and Hot Start DNA polymerases obtained from company R (lanes 1-16). Added to the lyophilized and ready-to-use mixtures was: 100 mM cellobiose (lanes 1-5), 200 mM cellobiose (lanes 6-10) or 200 mM trehalose (lanes 12-16). No substances were added to the lyophilized and ready-to-use mixture used in lane 11.

M: molecular weight marker "BenchTop PCR Markers", Promega.

PCR products: 268 bp: fragment of the human beta-globin gene; 240 bp; fragment of the *Plasmodium* spp 18s RNA gene.

Figure 14:
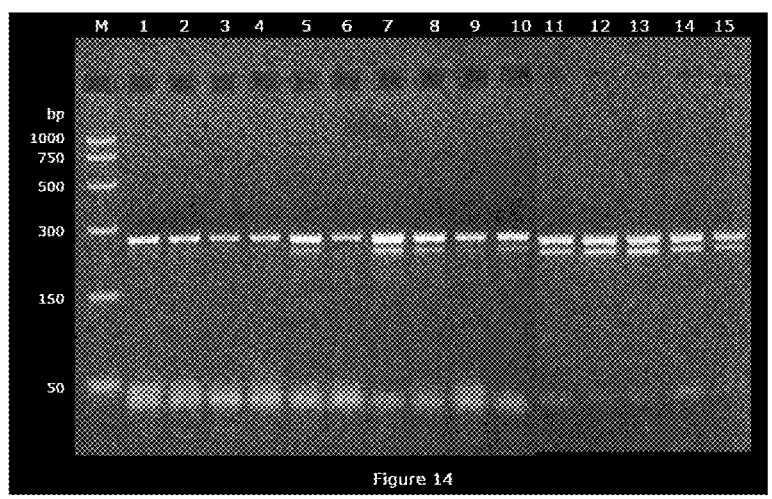

FIG. 14. Agarose gel electrophoretic pattern of lyophilized and ready-to-use amplification mixtures, containing cellobiose or trehalose, after preservation at 37° C. for two weeks. The lyophilized and ready-to-use mixtures contain reaction buffers and Hot Start DNA polymerases obtained from company R (lanes 1-15). Added to the lyophilized and ready-to-use mixtures was: 100 mM cellobiose (lanes 1-5), 200 mM cellobiose (lanes 6-10) or 200 mM trehalose (lanes 11-15).

M: molecular weight marker "BenchTop PCR Markers", Promega.

PCR products: 268 bp: fragment of the human beta-globin gene; 240 bp; fragment of the *Plasmodium* spp 18s RNA gene.

Figure 15:
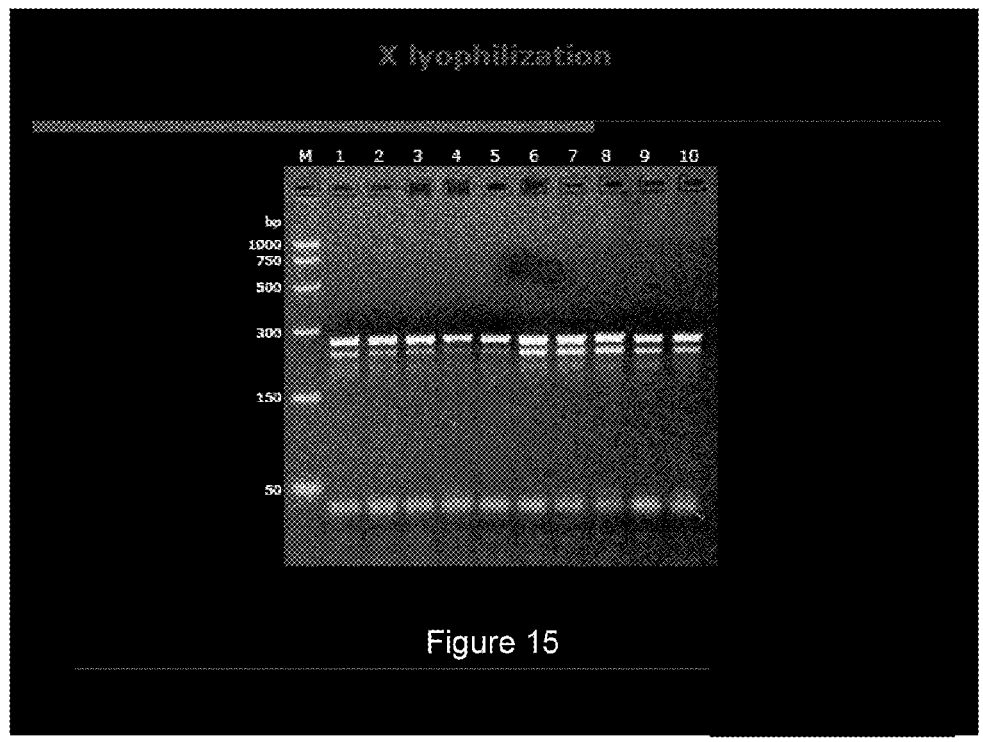

FIG. 15. Agarose gel electrophoretic pattern of lyophilized and ready-to-use amplification mixtures, containing cellobiose or trehalose, after preservation at 55° C. for: 24 hours (lanes 1 and 6), 48 hours (lanes 2 and 7), 72 hours (lanes 3 and 8), 96 hours or one week (lanes 5 and 10). The lyophilized and ready-to-use mixtures contain reaction buffers and Hot Start DNA polymerases obtained from company R (lanes 1-10).

M: molecular weight marker "BenchTop PCR Markers", Promega.

PCR products: 268 bp: fragment of the human beta-globin gene; 240 bp; fragment of the *Plasmodium* spp 18s RNA gene.

In all the figures, "M" corresponds to the lane of the molecular weight marker "Bench Top PCR Markers" by the Promega company; the fragments of said marker vary from 50 bp to 1000 bp.

FIG. 16. Agarose gel electrophoretic pattern of the wildtype (wt) DNA control sample (C1), a unknown DNA sample (C2), the mutant DNA control sample (C3) and the no template control (N) amplified products obtained with lyophilized and ready-to-use amplification mixtures and with the reference method.

FIG. 16a. Results before purification procedure of the amplified products.

FIG. 16b. Results after purification procedure of the amplified products.

FIG. 17. Direct sequencing results

FIG. 17a. Direct sequencing results of a wildtype (SEQ ID NO:1) and a mutant (SEQ ID NO:2) sequence amplified products obtained with lyophilized and ready-to-use amplification mixtures.

FIG. 17b. Direct sequencing results of a wildtype (SEQ ID NO:1) and a mutant (SEQ ID NO:2) sequence amplified products obtained with the reference method.

Figure 18B:
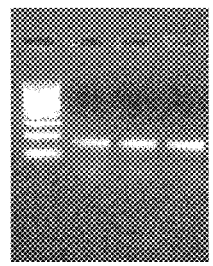
Figure 18B:
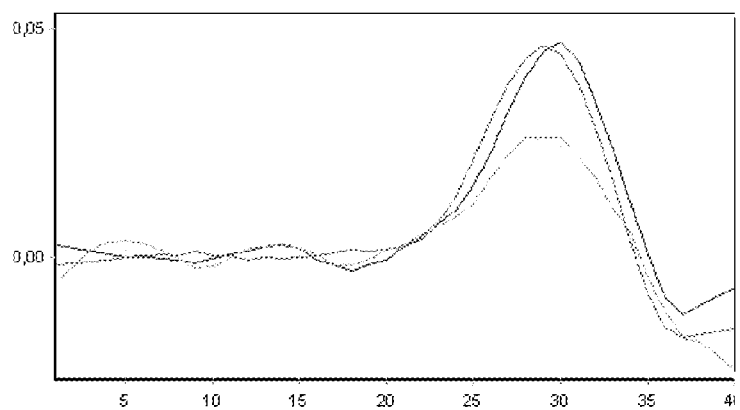

FIG. 18. PCR and Real time PCR

FIG. 18a (i). Agarose gel electrophoretic pattern of the wildtype (wt) DNA control sample (C1), a unknown DNA sample (C2), and the mutant DNA control sample (C3) amplified products obtained with lyophilized and ready-to-use amplification mixtures;

FIG. 18a (ii). Real time PCR take off curves obtained with lyophilized and ready-to-use amplification mixtures;

FIG. 18a (iii). Real time PCR quantitative comparative results obtained with lyophilized and ready-to-use amplification mixtures.

FIG. 18b (i). Agarose gel electrophoretic pattern of the wildtype (wt) DNA control sample (C1), a unknown DNA sample (C2), the mutant DNA control sample (C3) and the no template control (N) amplified products obtained with the reference method;

FIG. 18b (ii). Real time PCR take off curves obtained with the reference method;

FIG. 18b (iii). Real time PCR quantitative comparative results obtained with the reference method.

FIG. 19a. Melting curve analysis results obtained with lyophilized and ready-to-use amplification mixtures;

FIG. 19b. Melting curve analysis results obtained with the reference method.

FIG. 20a. High Resolution Melting Analysis (HRM) results obtained with lyophilized and ready-to-use amplification mixtures;

FIG. 20b. High Resolution Melting Analysis (HRM) results obtained with the reference method.

Figure 21:
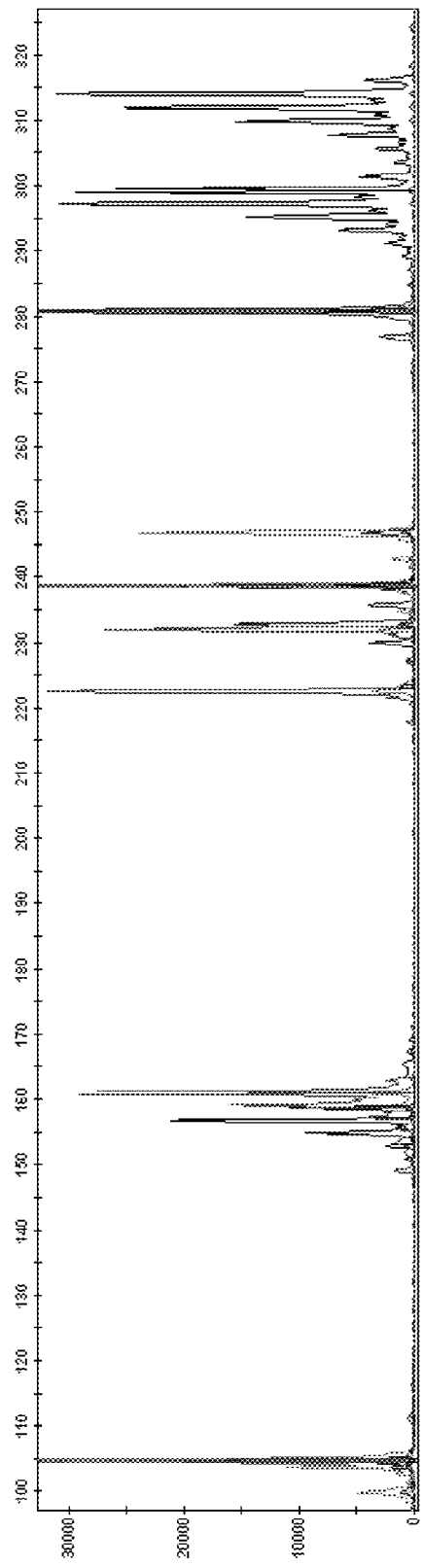

FIG. 21a. Quantitative Fluorescence (QF) pherogram, results obtained with lyophilized and ready-to-use amplification mixtures;

FIG. 21b. Quantitative Fluorescence (QF) pherogram, results obtained with the reference method;

DETAILED DESCRIPTION OF THE INVENTION

Definitions

In order to facilitate comprehension of the invention, some terms are defined below.

The term "stabilizing agent" means an agent which, when added to a biologically active material, can prevent or retard loss of activity over time as compared to preserving the material in the absence of the stabilizing agent.

The term "polymerase" refers to an enzyme or to its active fragments able to synthesize nucleic acid strands (RNA or DNA) from an RNA or DNA template and the availability of ribonucleoside triphosphates or deoxynucleoside triphosphates.

The term "polymerase activity" refers to the ability of an enzyme to synthesize strands of nucleic acid (RNA or DNA) starting from ribonucleoside triphosphates or deoxynucleoside triphosphates.

The terms: "buffer" or "buffering agents" refer to substances or preparations which, when added to a solution, confer resistance to pH changes thereto.

The term "reducing agent" refers to an electron donor, i.e. a material that donates electrons to a second material to reduce the oxidative state of one or more of the atoms of the second material.

The term "solution" refers to a mixture, either aqueous or non-aqueous.

The term "buffer solution" refers to a solution containing a buffering agent.

The term "reaction buffer" refers to a buffer solution in which an enzyme reaction is developed.

The term "storage buffer" refers to a buffer solution in which an enzyme is preserved.

The term "template" refers to a nucleic acid originating from a biological sample which is analyzed for presence of the "target".

The term "target" refers, when used in reference to the molecular biology techniques, to the region of the nucleic acid recognized by the specific primers used for the amplification reaction. In the case of PCR for diagnostic use, the target DNA consists of the nucleic acid of the pathogenic agent.

The term "primers" or triggers refers to synthesized oligonucleotides able to act as triggers for synthesis when used under conditions that induce nucleic acid synthesis (presence of nucleotides and polymerase).

The term dNTPs (deoxynucleoside triphosphates) refers to a mixture of deoxyadenosine, deoxythymidine, deoxyguanosine and deoxycytidine in which the concentrations of each of the deoxynucleoside triphosphates are indicated.

The term "PCR product" or "amplified fragment" refers to a DNA fragment, generally in a double helix, resulting from two or more PCR cycles, i.e. chain polymerization, following the steps of denaturation of the template DNA chain, annealing of the specific primers thereto and extension or elongation of the chain complementary to the template DNA, starting from the OH terminal of the primer.

Detailed Description

The present invention relates to the use of the disaccharide cellobiose for stabilizing nucleic acid polymerization enzymes, specifically DNA polymerase, Hot Start DNA polymerase, RNA polymerase, or their active fragments, during lyophilization (or exsiccation), and to preserve them in this form over time.

In a preferred aspect the present invention relates to a exsiccated or lyophilized composition suitable for being diluted with an appropriate solvent, comprising a nucleic acid polymerization enzyme stabilized to withstand lyophilisation and storage at a temperature up to 55° C., characterized in that said composition has a nucleic acid polymerization enzyme concentration in the range from 0.01 to 250 Units, cellobiose in a concentration in the range from 50 mM (17.115 g/L) to 500 mM (171.15 g/L) and a buffer, wherein the buffer is preferably Tris HCl. Said nucleic acid polymerization enzyme is a DNA polymerase preferably selected from the group consisting of Taq Polymerase, Hot Start polymerase or their active fragments.

Said composition is also referred to as a "lyophilized and ready-to-use amplification mixture" or "Universal Master Mix".

The exsiccated or lyophilized composition is obtained by lyophilization (or exsiccation) from a liquid or frozen mixture, in which cellobiose is in a concentration comprised between 50 mM and 500 mM or comprised between 150 mM (51.345 g/L) and 250 mM (85.575 g/L) or preferably 250 mM and in which the nucleic acid polymerization enzyme concentration is in the range from 0.01 to 250 Units or preferably at least 2 Units. The cellobiose used for the lyophilization is preferably of analytical grade.

In a preferred aspect of the present invention regards a composition suitable for being diluted with an appropriate solvent, comprising a nucleic acid polymerization enzyme stabilized to withstand lyophilisation and storage at a temperature up to 55° C., characterized in that said composition has a nucleic acid polymerization enzyme concentration in the range from 0.01 to 250 Units, cellobiose in a concentration in the range from 50 to 500 mM, a buffer, dNTPs, KCl and $MgCl_2$, wherein the buffer is preferably Tris HCl.

The composition comprises preferably according to an embodiment of the enzyme in ready-to-use form in PCR, even more preferably at least one of the following reagents:

i. stabilizers selected from the group consisting of: surfactants, ionic or non-ionic detergents, such as NP40, Tween 20 or Triton-X100 and/or non-reducing sugars, such as: dextrose, sucrose, trehalose;

ii. reducing agents selected from the group consisting in: β-mercaptoethanol, DTT or ammonium sulphate;

iii. at least one probe, optionally labelled.

Optionally, when the lyophilized composition is used for Real-Time PCR, it can comprise probes, possibly labelled with, for example, fluorescent groups selected from the group consisting of TaqMan Probes®, Molecular Beacons®, Scorpions Probes®, HiBeacon Probes®, or other probes usable for Real-Time PCR.

When the composition of the invention is reconstituted in water or in a buffer system containing DNA, the cellobiose is in a concentration comprised between 50 mM and 500 mM, or comprised between 150 mM and 250 mM or preferably 250 mM, and at this concentration it does not interfere with the gene amplification reaction.

Even more preferably the composition consists of ready-to-use lyophilized or exsiccated preparations, containing all the reagents described in the preferred embodiment and prepared in advance for gene amplification directly after reconstitution in the single container, such as a tube or microplate, or in bulk.

The invention further relates to the use of the composition for the amplification of nucleic acids, which can be carried out in an automated fashion, in particular for molecular biology applications such as, but not limited to PCR, Real Time PCR, Melting curve analysis, High Resolution Melting analysis, Sequencing, Quantitative Fluorescent PCR, Multiplex PCR, Whole Genome Amplification, Isothermal amplification.

The invention also provides a ready to use product comprising the exsiccated or lyophilized composition according to the invention and a solvent for reconstituting said composition.

The lyophilized composition prepared according to the invention results in a considerable simplification of the PCR process performed therefrom, hence enabling contamination problems to be prevented, but mainly allowing a considerable flexibility with regard to the nucleic acid volumes required for the reaction, with a consequent notable increase in test robustness. This last aspect is particularly interesting in forensic science since a larger volume of nucleic acid may be used with the lyophilized compositions.

Moreover, the considerable increase in room temperature stability of the polymerase-containing composition means that applications of specific interest to the veterinary and human diagnostics fields, and the food analysis fields, are made possible, particularly if carried out in not very well-equipped facilities. These uses are therefore particularly preferred. The increase in stability of composition to storing at a temperature up to 55° C. also allows more flexibility for shipment and storage.

The invention still further relates to a process for the amplification of nucleic acids comprising the steps of:
v. reconstituting the composition of the invention in water or in a buffer;
vi. adding primers specific for a target DNA;
vii. adding a nucleic acid template;
viii. optionally adding one or more of the reagents selected from the group consisting in: KCl, $MgCl_2$, dNTPs, at least one optionally labelled probe, reducing agents and further stabilizers.

A further aspect of the invention relates to a method for preparing an exsiccated or lyophilized composition containing a stable polymerase at room temperature, preferably a DNA polymerase, and even more preferably a Taq Polymerase or still more preferably a Hot Start Polymerase essentially characterized by mixing said enzyme (or said enzymes) with cellobiose at concentrations between 50 mM and 500 mM, preferably between 150 mM and 250 mM in a lyophilization and storage buffer which can consist, for example, of Tris-HCl according to a protocol defined as "minimal" and subjecting the solution to lyophilization or exsiccation, preferably after rapid freezing.

The enzyme is added in a quantity of at least 1-5 IU: the minimal method also provides for addition of a salt, preferably selected from the group consisting of: KCl, $MgCl_2$, prior to lyophilization.

One of the advantages of the present invention is that the system stabilized by means of cellobiose adapts to all DNA polymerases from the various manufacturing companies.

Furthermore, the cellobiose is produced by a system of enzymatic hydrolysis starting from cellulose, a molecule consisting of long chains of glucose (sugar) of plant origin. The plant origin guarantees the absence of possible nucleic acid contaminants originating from bacterial contamination which is likely when, as in the case of trehalose, production involves the use of bacterial cultures for its synthesis.

There are many systems, all being applicable, for mixing the enzyme or enzymes and the stabilizer (cellobiose) either alone or with the other components. For example, a method where a solution containing the dissolved enzyme is added with the stabilizer, or a method in which a solution containing the enzyme is mixed with a second solution containing the stabilizer, or a method in which the enzyme is dissolved in a solution containing the stabilizer and another method in which a solution containing both the enzyme and the stabilizer is preserved either as a liquid or lyophilized.

Lyophilization is carried out according to criteria known to the expert of the art. An example of a possible protocol for lyophilization is the following:

Long Lyophilization Protocol:
Gradient from +20° C. to −40° C. in 5 minutes
−40° C. for 3 hours
Gradient from −40° C. to −10° C. in 30 minutes
−10° C. for 4 hours
Gradient from −10° C. to +10° C. in 15 minutes
+10° C. for 2 hours
Gradient from +10° C. to +30° C. in 15 minutes
+30° C. for 4-8 hours.

Lyophilization can be carried out according to the following shorter protocol, also applicable in reason of the small volumes involved. An example of a possible protocol for lyophilization is the following:

Short Lyophilization Protocol:
Gradient from +20° C. to −40° C. in 5 min
−40° C. for 30 min
Gradient from −40° C. to −10° C. in 15 min
−10° C. for 30 min
Gradient from −10° C. to +10° C. in 15 min
+10° C. for 60 min
Gradient from +10° C. to +30° C. in 15 min
+30° C. for 60 min The Short Freeze-drying Protocol is particularly indicated when the enzyme is not stored in glycerol, while the Long Freeze-drying Protocol can be used whether or not the enzyme is stored in glycerol.

In a further and preferred embodiment, particularly for diagnostic use, the invention relates to a method for preparing the composition for lyophilizing a polymerase in a ready-to-use form, which comprises the following steps:

mixing the enzyme with cellobiose in concentrations comprised between 50 and 500 mM, preferably between 150 and 250 mM, or vice versa, in a lyophilization and storage buffer which can consist for example of Tris-HCl, in accordance with a protocol defined as "minimal",
addition of salts preferably selected from the group consisting of KCl, Tris-HCl, $MgCl_2$,
optional addition of:
dNTPs,
primers, preferably at least one 5' primer (forward) and one 3' primer (reverse), specific for the target DNA present in the sample,
optional addition of a further stabilizer selected from the group consisting of: ionic or non-ionic detergents, such as NP40, Tween-20 and/or non-reducing sugars, such as: dextrose, sucrose, trehalose, or a reducing agent such as DTT or β-mercaptoethanol,
lyophilization (or exsiccation) as indicated above preferably after rapid freezing, and preservation of the enzyme in this form.

The method can also include the addition of a control DNA for the polymerization chain reaction and specific primers prior to lyophilization.

The term stabilizers means either detergents (or surfactants) such as: NP-40 (alkyl-phenol ethoxylate), Tween-20 (sorbitan-polyoxyethylate monolaurate) or Triton-X100 or analogues thereof, and non-reducing sugars such as dextrose, sucrose, trehalose.

The further reagents can be added singly or pre-mixed in a reaction mixture, such as that supplied with the enzyme by the manufacturer, being n times more concentrated (generally ×10) than the final concentration used for the polymerization reaction.

The enzyme in lyophilized form, possibly ready-to-use, can be maintained at room temperature for several months.

The lyophilization and stability of the enzyme in this form, possibly combined with specific reagents for the subsequent polymerase chain reaction, enable containers to be prepared (tube, tests tube or microplate) comprising the mixture in exsiccated and ready form to be used after reconstitution with a buffer or with water, possibly containing the DNA/RNA template in the sample which, if present, has to be amplified.

This aspect hence enables the standardization of subsequent amplification reactions for all uses of the present invention comprising the diagnostic use.

Furthermore, the lyophilization and preservation protocols are suitable for both chain amplification reactions by classic and Real-Time PCR, and therefore for both quantitative- and qualitative-type uses.

One of the advantages of the present invention is that the stabilizer used (cellobiose) is effective for both lyophilization and preservation of the enzyme, whereas stabilizers of the known art are generally used for either one or the other purpose. Though compatible with other molecules used for this purpose, the use of cellobiose makes the use of other "stabilizing" molecules unnecessary for the various stages. In addition, because cellobiose is less soluble than trehalose, it is also expected to be less hygroscopic and thus able to confer a superior shelf-life to the lyophilized product.

Furthermore, the invention comprises kits for PCR amplification of a DNA sample comprising the composition according to the invention and optionally instructions for the reconstitution and use of the enzyme in a polymerase chain reaction.

A particularly preferred embodiment of the invention consists of the use of cellobiose for the preservation of a nucleic acid polymerase during freeze-drying and for long term storage at a temperature up to 55° C.

Said lyophilized composition for single reaction is suitable for amplifying a DNA sample of at least 1 ng, after reconstitution in a minimal volume of a few μl (2-50, preferably 5-30).

The lyophilisate can also be directly reconstituted in a buffer containing the DNA of the sample. The concentration of the various reagents in the lyophilized composition in ready-to-use form, or in the reaction mix to be added immediately after reconstitution of the enzyme, must be such as to be optimal, after reconstituting the composition with water or buffer in a suitable volume, for DNA amplification by PCR, i.e. preferably in which KCl is in a concentration between 20 and 150 mM, $MgCl_2$ is in a concentration between 0.5 and 5 mM, specific primers for the polymerization reaction and amplification of the target DNA are in a concentration between 0.05 and 0.2 mM and dNTPs are in a concentration between 50 and 200 mM. Such a kit, containing the enzyme in lyophilized form, can be maintained at room temperature.

Another aspect of the invention relates to the use of cellobiose for the preservation of a DNA polymerase, preferably a Hot Start DNA polymerase during freeze-drying and Storage at a temperature up to 55° C.

As noted above, lyophilization of the enzyme and its stability even in the form of a ready-to-use reaction mix, either in single doses or in bulk, allows the chain amplification reaction conditions to be more standardized. Therefore a preferred use of the composition of the invention and the lyophilization process made possible by the present invention, concerns the preparation of diagnostic kits specifically for determining the presence of parasitic agents in biological fluids or tissues. Therefore, particularly preferred are lyophilized or exsiccated compositions in ready-to-use form, comprising, in addition to the enzyme and cellobiose and the aforedefined reagents (e.g. salts and dNTPs), specific primers for the target DNA of *Plasmodium* (one pair for each of the species *falciparum, malariae, vivax* and *ovale*) preferably designed in the conserved region of 18sRNA, or of *Leishmania*, with primers preferably designed in the conserved region of 18sRNA or otherwise of *Toxoplasma*, with primers preferably designed in the highly repeating region HRE, for diagnostic identification of said pathogenic agents in a DNA sample.

Each lyophilized composition, in ready-to-use form, also comprises an internal amplification control preferably corresponding to a primer pair of a gene normally expressed in the reference system, such as preferably the human beta-globin gene and, optionally, a control DNA template for the amplification.

Additional components preferably present in the composition produced in ready-to-use form are: KCl in a final concentration after reconstitution comprised between 20 and 150 mM and $MgCl_2$ between 0.05-5 mM, preferably in a 5-20 mM Tris-HCl buffer (pH 8.0), optionally specific primers for amplification of the DNA whose presence is required to be detected in the sample, in a concentration of 0.05-0.2 mM, and dNTPs in a concentration comprised between 50 and 200 mM. The implementation of the invention is described herein in some specific non-limiting examples.

EXPERIMENTAL PART

Materials

Methods. The lyophilization compositions described in the experimental part generally contain, where not otherwise and separately indicated, the following specific reagents added at the appropriate time: a DNA polymerase (within the range of 1 to 5 units), the reaction buffer supplied by the manufacturer, $MgCl_2$, dNTPs and primers.

In particular, in the examples given for this invention, the reaction mixture contains primers for amplifying two regions in the DNA: 1) a fragment of 240 bp (base pairs) designed in the 18s ribosomal RNA gene of *Plasmodium* spp. (target DNA), 2) a 268 bp fragment designed in the human β-globin gene, used as internal amplification control (DNA control), salts and dNTPs.

After the lyophilization, about 10 ng (nanograms) of genomic DNA extracted by the silica gel method from peripheral blood positive for *Plasmodium falciparum* was added to the lyophilized mixture and the final volume brought to 25 μl (microlitres) with sterile distilled water.

After an initial denaturation at 94° C. for 2 minutes, amplification cycles were performed consisting of denaturation (94° C. for 2 minutes), annealing (55° C. for 30 seconds) and extension (72° C. for 45 seconds). To complete the reaction 40 cycles as aforedescribed were performed.

One of the lyophilization protocols used consisted of:
Gradient from +20° C. to −40° C. in 5 minutes
−40° C. for 3 hours
Gradient from −40° C. to −10° C. in 30 minutes
−10° C. for 4 hours
Gradient from −10° C. to +10° C. in 15 minutes
+10° C. for 2 hours
Gradient from +10° C. to +30° C. in 15 minutes
+30° C. for 4-8 hours.

Example 1

Comparison between DNA Polymerase and Hot Start Polymerase

With the aim of identifying the type of DNA polymerase that maintains good polymerase activity after the lyophilization process, we compared a commercial DNA polymerase with two Hot Start DNA polymerases available from two different manufacturers.

Figure 1:
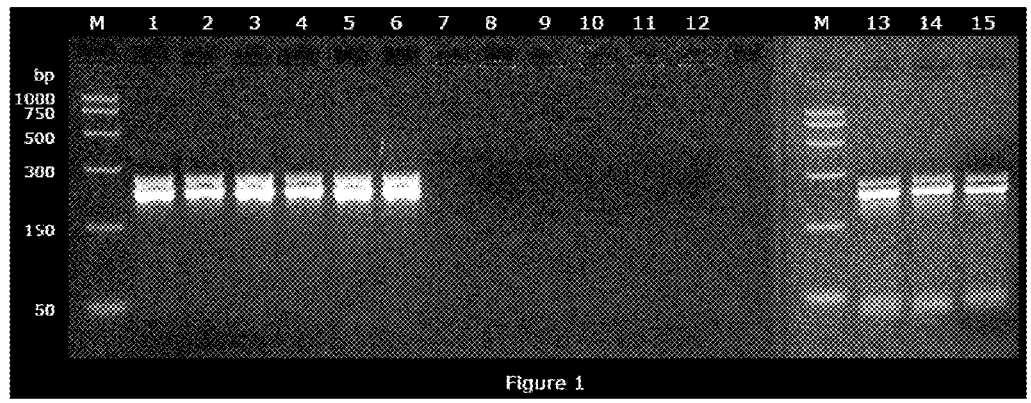
FIG. 1. Agarose gel electrophoretic pattern of lyophilized and ready-to-use amplification mixtures, immediately following completion of the lyophilization process. Lanes 1-6: PCR products amplified with lyophilized and ready-to-use compositions prepared with Hot Start polymerase from company X; volume before lyophilization: 25 µl (lanes 1-3) or 9.1 µl (lanes 4-6). Lanes 7-12: amplification products obtained with the lyophilized and ready-to-use mixtures prepared with Hot Start DNA polymerase of company Y; volume before lyophilization: 25 µl (lanes 7-9) or 7.5 µl (lanes 10-12). Lanes 13-15: PCR products obtained with lyophilized and ready-to-use amplification mixtures prepared with a polymerase obtained from company X; volume before lyophilization: 25 µl.

In FIG. 1, lanes 1 to 6 show PCR products amplified with lyophilized and ready-to-use mixtures prepared with Hot Start polymerase from company X; in particular the reaction volumes before lyophilization correspond to 25 μl for lanes 1 to 3, and 9.1 μl for lanes 4 to 6. Lanes 7 to 12 correspond to amplification products obtained with the lyophilized and ready-to-use mixtures prepared with Hot Start DNA polymerase from company Y; in particular the reaction volumes before lyophilization correspond to 25 μl for lanes 7 to 9, and 7.5 μl for lanes 10 to 12. Lanes 13 to 15 correspond to the PCR products obtained with the lyophilized and ready-to-use amplification mixtures prepared with polymerase obtained from company X; the reaction volumes are 25 μl.

No stabilizer was added to the reaction mixture before lyophilization.

As shown in FIG. 1 in which the amplification products were analyzed immediately after the lyophilization process, it can be seen from lanes 7 to 12 that the mixture containing the Hot Start DNA polymerase obtained from company Y does not enable amplification of the two expected amplification products, whereas both the polymerases, Hot Start and non-Hot Start (respectively 1 to 6 and 13 to 15) obtained from company X, maintain their polymerase activity after lyophilization.

Company X includes within its own reaction buffer substances which physically increase solution density, they being defined solely and generically as stabilizers.

With the aim of evaluating the heat stability of lyophilized and ready-to-use mixtures for PCR, prepared with the polymerases obtained from company X, the same mixtures were preserved at room temperature and at 37° C. for 3 weeks.

Photograph 2 shows the amplification products obtained with the amplification mixtures containing Hot Start DNA polymerase of company X; in particular the final volumes before lyophilization of the mixtures used for PCR correspond to 25 μl for lanes 1 to 4 and 9.1 μl for lanes 5 to 8. Lanes 9 to 12 show the amplification products obtained with lyophilized and ready-to-use reaction mixtures containing DNA polymerase from company X; the reaction volumes before lyophilization correspond to 25 μl. Said lyophilized reaction mixtures were preserved at room temperature (lanes 1 to 3, 5 to 7, 9 to 11) or at 37° C. (lanes 4, 8 and 12) for 3 weeks after lyophilization.

As shown in the photograph, after 3 weeks at room temperature, the amplification products obtained with the mixtures containing hot Start DNA polymerase (lanes 1 to 3 and 5 to 7) prove to be more intense than those obtained with simple DNA polymerase (lanes 9 to 11). Moreover, Hot Start DNA polymerase does not result in the formation of primer dimers, in contrast to the other polymerase.

In conclusion, after 3 weeks' preservation at 37° C., the Hot Start DNA polymerase maintained its enzyme activity (lanes 4 and 8) while simple DNA polymerase did not (lane 12).

Therefore, it is absolutely certain that: 1) use of stabilizers is critical for preserving the enzyme activity of DNA polymerase during the lyophilization process, 2) Hot Start DNA polymerase is more suited than normal DNA polymerase for amplification efficiency, but not for the lyophilization process as both categories of DNA polymerase exhibit similar behaviour, i.e. they require stabilizers for the lyophilization.

Finally, in this experiment, 2 different volumes were tested before the lyophilization step (25 and 9.1 μl) without any change being noted in the results.

Example 2

Comparison between Different Hot Start DNA DNA Polymerases

In the following experiment, lyophilized and ready-to-use amplification mixtures were prepared containing Hot Start DNA polymerases obtained from 4 different companies (W, X, R, Y), each combined with their 4 reaction buffers or with added stabilizers such as NP-40, Tween-20 and sucrose, for a total of 19 combinations.

In FIGS. 3 and 4, lanes 1 to 4, 5 to 8, 9 to 12 and 13 to 19 represent products amplified by PCR using the lyophilized ready-to-use mixtures containing respectively the reaction buffers obtained from companies W, X, R or Y. In the same figures, lanes 1, 5, 9 and 13 correspond to the amplification products obtained with lyophilized and ready-to-use amplification mixtures containing Hot Start DNA polymerases obtained from company W; lanes 2, 6, 10, 14, 17, 18 and 19 correspond to amplification products obtained with lyophilized and ready-to-use amplification mixtures containing Hot Start DNA polymerases obtained from company Y; lanes 3, 7, 11 and 15, correspond to amplification products obtained with lyophilized and ready-to-use amplification mixtures containing Hot Start DNA polymerases obtained from company X; lanes 4, 8, 12 and 16 correspond to amplification products obtained with lyophilized and ready-to-use amplification mixtures containing Hot Start DNA polymerases obtained from company R. In FIGS. 3 and 4, lanes 17, 18 and 19 correspond to amplification products obtained with lyophilized and ready-to-use mixtures also containing respectively 0.25% NP-40 and 0.25% Tween-20, 100 mM sucrose and 0.25% NP-40, 0.25% Tween-20 and 100 mM sucrose.

The PCR products presented in FIG. 3 were amplified using the lyophilized and ready-to-use mixtures immediately after completion of the lyophilization protocol. In contrast, FIG. 4 shows results of the same mixtures preserved at room temperature for 6 months.

As clearly shown in FIG. 3, the mixtures containing the reaction buffer of company X, which were monitored just after lyophilization, maintained their enzyme activity in 3 out of 4 polymerases, whereas, for the fourth, activity was only partially maintained.

The mixtures prepared with the reaction buffer of companies W or R preserved the activity of 1 out of 4 polymerases. Finally, in the presence of the reaction buffer obtained from company Y, no amplification corresponding to the two expected fragments was seen; a residual enzyme activity could only be seen in the presence of 100 mM sucrose. In addition, the lyophilized and ready-to-use amplification mixtures were preserved at room temperature for 6 weeks, before carrying out the amplification by PCR. As shown in FIG. 4, only the lyophilized mixtures prepared with the reaction buffer of company X were able to preserve the enzyme activity of three out of the four Hot Start DNA polymerases used.

These results emphasize the importance of including a stabilizer in the PCR reaction mixture during the lyophilization process in order to preserve the enzyme activity of polymerases.

Example 3

Stability of the Lyophilized and Ready-to-Use Compositions for PCR, Containing 250 mM Sucrose With the aim of evaluating improvement in the stability of the lyophilized PCR reaction mixtures, the effect of the presence of 250 mM sucrose in the storage buffer, in the reaction buffer or in both was initially evaluated. Two different Hot Start DNA polymerases obtained from two different companies were evaluated.

In FIGS. 5 and 6, lanes 1 to 7 and lanes 8 to 21 represent the amplification products obtained with lyophilized and ready-to-use reaction mixtures containing Hot Start DNA polymerases obtained from company X or R respectively. In FIGS. 5 and 6, lanes 1, 8 and 9, correspond to amplification products obtained with lyophilized and ready-to-use reaction mixtures prepared with the reaction buffer of company X; lanes 2 and 3 and lanes 14 to 17, correspond to amplification products obtained with lyophilized and ready-to-use reaction mixtures prepared with the reaction buffer of company W; lanes 4 and 5 and lanes 10 to 13, correspond to amplification products obtained with lyophilized and ready-to-use reaction mixtures prepared with the reaction buffer of company R; lanes 6 and 7 and lanes 18 to 21, correspond to amplification products obtained with lyophilized and ready-to-use reaction mixtures prepared with the reaction buffer of company Y. In FIGS. 5 and 6, lanes 3, 5, 7, 11, 15 and 19, represent amplification products obtained with lyophilized and ready-to-use reaction mixtures prepared by adding 250 mM sucrose to the reaction buffer; lanes 9, 12, 16 and 20, represent amplification products obtained with lyophilized and ready-to-use reaction mixtures prepared by adding 250 mM of sucrose to the storage buffer; lanes 13, 17 and 21, represent amplification products obtained with lyophilized and ready-to-use reaction mixtures prepared by adding 250 mM sucrose to the reaction buffer and the storage buffer.

The amplification products shown in FIG. 5 were amplified with the lyophilized and ready-to-use reaction mixtures utilized immediately after completion of the lyophilization process whereas the results of FIG. 6 are the same as those of FIG. 5 but after preserving the lyophilized and ready-to-use mixtures at room temperature for 8 weeks.

As highlighted in FIG. 5, the presence of 250 mM sucrose in the reaction buffer but not in the storage buffer is essential for maintaining enzyme activity during and after the lyophilization process. After 8 weeks of preservation at room temperature, preservation of enzyme activity was only possible in half the cases (5 out of 10) (FIG. 6). Consequently, it can be concluded that sucrose has a protective action toward enzyme activity, though it is not effective for long-term preservation.

Example 4

Stability of the Lyophilized Compositions Prepared with Different Stabilizing Substances With the aim of comparing the heat stability of the lyophilized and ready-to-use amplification mixtures containing different stabilizers, elements such as disaccharides, polysaccharides or carbohydrates were utilized, they being added to the amplification mixtures prepared as described in the introduction.

In FIGS. 7 and 8, lanes 1 to 5 and lanes 6 to 10, represent amplification products obtained with lyophilized and ready-to-use amplification mixtures containing, respectively, Hot Start DNA polymerases obtained from companies W or R. In FIGS. 7 and 8, lanes 1 and 6, 2 and 7, 3 and 8, 4 and 9, and 5 and 10 correspond to lyophilized and ready-to-use amplification mixtures containing respectively: no stabilizer; 200 mM trehalose, 250 mM sucrose, 200 mM maltose and 0.025% agarose.

The amplification products shown in FIG. 7 were obtained with the lyophilized and ready-to-use amplification mixtures immediately after completion of the lyophilization process whereas the results shown in FIG. 8 are the same as those of FIG. 7 but after preserving the lyophilized and ready-to-use reaction mixtures at 37° C. for one week.

The presence of 250 mM sucrose, 200 mM trehalose, 200 mM maltose and 0.025% agarose in the lyophilized and ready-to-use reaction mixture was initially evaluated by using two different Hot Start DNA polymerases obtained from two different companies. As highlighted in FIG. 7, the presence of trehalose, sucrose, and maltose (lanes 2 and 7, 3 and 8 and 4 and 9 respectively) in the lyophilized and ready-to-use reaction mixtures enables the enzyme activity of both enzymes to be preserved, although the action appears to be less effective on the enzyme obtained from company R (lanes 7, 8 and 9); this is particularly evident for sucrose (lane 8). No amplification band was noted for agarose (FIG. 7, lanes 5 and 10). In addition, the lyophilized and ready-to-use mixtures were preserved at 37° C. for one week before being processed by PCR. The lyophilized mixtures containing 200 mM trehalose maintained intact the enzyme activity of both the Hot Start DNA polymerases (FIG. 8, lanes 2 and 7) whereas those with 250 mM sucrose and 0.025% agarose did not (FIG. 8, lanes 3 and 8, 5 and 10 respectively).

The maltose at 200 mM maintained the activity of one polymerase (FIG. 8, lane 9), but only partially maintained that of the other.

The action of 250 mM trehalose, 6.6% dextrose, 200 mM cellobiose (Fluka Analytical 22150 D-(+)-Cellobiose) and 6.6% amylopectin, added to the reaction mixtures before being lyophilized, was then evaluated on the same two polymerases.

In FIGS. 9 and 10, lanes 1 to 5 and lanes 6 to 10, represent the amplification products obtained with lyophilized and ready-to-use reaction mixtures prepared with the Hot Start DNA polymerases obtained respectively from company W or R.

In FIGS. 9 and 10, lanes 1 and 6, 2 and 7, 3 and 8, 4 and 9, 5 and 10, correspond to lyophilized and ready-to-use reaction mixtures containing: no stabilizer, 250 mM trehalose, 6.6% dextrose, 200 mM cellobiose or 6.6% amylopectin, respectively. The results in FIG. 9 correspond to the lyophilized mixtures processed immediately after having completed the lyophilization process, whereas the results shown in FIG. 10 correspond to the reaction mixtures with the same characteristics prepared at the same time as the previous ones, but preserved at 37° C. for one week.

As shown in FIG. 9, introducing trehalose and cellobiose into the lyophilized reaction mixture preserved the enzyme activity of both the Hot Start DNA polymerases (lanes 2 and 7, 4 and 9 respectively) whereas the dextrose and amylopectin protected only one of the two enzymes (lanes 3 and 8, 5 and 10 respectively). In addition, reaction mixtures with the same characteristics and prepared at the same time as the previous ones, were preserved for one week at 37° C. before being processed by PCR. The lyophilized reaction mixtures containing 250 mM trehalose and 200 mM cellobiose as stabilizers protected the enzyme activity of both polymerases (FIG. 10, lanes 2 and 7, 4 and 9, respectively), whereas 6.6% dextrose and 6.6% amylopectin did not preserve it (FIG. 10, lanes 3 and 8, 5 and 10 respectively).

In addition, 0.5% albumin, 2% albumin and 3% lactose were also evaluated but results comparable to those gained with trehalose and cellobiose were not obtained.

Accordingly, it was clearly demonstrated that only cellobiose and trehalose provide protection to DNA polymerase.

Example 5

Evaluating the Optimal Concentration of Cellobiose for Stabilizing Lyophilized Compositions With the aim of identifying the most effective cellobiose concentration in preserving the enzyme activity of DNA polymerase, lyophilized and ready-to-use reaction mixtures were prepared as described in the introduction containing increasing concentrations of cellobiose.

The analyzed concentrations range from 0 to 700 mM of cellobiose.

In FIGS. 11 and 12, lanes 1 to 13 represent amplification products obtained with lyophilized reaction mixtures containing added cellobiose at a concentration of, respectively: 0, 50, 100, 150, 200, 250, 300, 350, 400, 450, 500, 600, and 700 mM.

The amplification products of FIG. 11 were obtained by using the lyophilized reaction mixture immediately after completing the lyophilization process, whereas the results of FIG. 12 correspond to reaction mixtures with the same characteristics and prepared at the same time as the previous ones, but preserved at 37° C. for two weeks.

As shown in FIGS. 11 and 12, the cellobiose concentrations which best preserve the enzyme activity of the polymerases lies within the range from 150 to 250 mM, even after preservation at 37° C. for one week (FIG. 12).

Accordingly, it was demonstrated that cellobiose provides the best stability to lyophilized and ready-to-use reaction mixtures within the concentration range from 150 to 250 mM.

Example 6

Evaluating the Time Stability of Lyophilized and Ready-to-use Compositions Containing Trehalose or Cellobiose as Stabilizers With the aim of identifying the time stability of lyophilized and ready-to-use mixtures containing trehalose or cellobiose, lyophilized ready-to-use reaction mixtures were prepared as described in the introduction, but with added 200 mM cellobiose or 200 mM trehalose. The mixtures were lyophilized before being subjected to amplification by PCR.

In FIG. 13, lanes 1 to 5, 6 to 10, 11 and 12 to 16 correspond to mixtures containing 100 mM cellobiose, 200 mM cellobiose, no stabilizer and 200 mM trehalose respectively.

The amplification products shown in FIG. 13 were obtained with the lyophilized reaction mixtures immediately after completion of the lyophilization process, whereas the results of FIG. 14 correspond to reaction mixtures with the same characteristics and prepared at the same time as the previous ones, but preserved at 37° C. for two weeks.

In FIG. 14, lanes 1 to 5, 6 to 10, 11 to 15 correspond to the lyophilized mixtures containing 100 mM cellobiose, 200 mM cellobiose or 200 mM trehalose respectively. The amplification products shown in FIG. 15 were obtained with the lyophilized reaction mixture preserved at 55° C. respectively for: 24 hours, 48 hours, 72 hours, 96 hours and one week (lanes 1, 6 and 11; 2, 7 and 12; 3, 8 and 13; 4, 9 and 14; 5, 10 and 15 respectively).

In FIG. 15, lanes 1 to 5 represent the agarose gel electrophoretic pattern of lyophilized and ready-to-use amplification mixtures, containing cellobiose or trehalose, after preservation at 55° C. for 24 hours (lanes 1 and 6), 48 hours (lanes 2 and 7), 72 hours (lanes 3 and 8), 96 hours or one week (lanes 5 and 10). The lyophilized and ready-to-use mixtures contain reaction buffers and Hot Start DNA polymerases obtained from company R (lanes 1-10). M: molecular weight marker "Bench Top PCR Markers", Promega.

PCR Products: 268 bp: fragments of the human beta-globin gene; 240 bp: fragment of the *Plasmodium* spp 18s RNA gene.

In all the figures, "M" corresponds to the lane of the molecular weight marker "Bench Top PCR Markers" by the Promega company; the fragments of said marker vary from 50 bp to 1000 bp.

As shown in FIG. 13, the stabilizers present in the lyophilized and ready-to-use reaction mixtures of this example preserve the polymerase activity very well. The lyophilized reaction mixtures were also preserved at 37° C. for one week before being processed with PCR.

Even after exposure to this stress, the polymerases present in the lyophilized and ready-to-use reaction mixtures containing 200 mM cellobiose (FIG. 14, lanes 6 to 10) maintained intact their enzyme activity, as did those with added 200 mM trehalose, (FIG. 14, lanes 11 to 15). After two weeks of preservation at 37° C., with 200 mM cellobiose (FIG. 14, lanes 6 to 10) or 200 mM trehalose (FIG. 14, lanes 11 to 15), the enzymes maintained their activity.

Finally, reaction mixtures with the same characteristics and prepared at the same time as the preceding ones were preserved at 55° C. for 24 hours, 48 hours, 72 hours, 96 hours and one week (FIG. 15) then subjected to amplification by PCR.

The use of trehalose as a stabilizer (FIG. 15, lanes 6 to 10) enables enzyme activity of the Hot Start DNA polymerases to be protected, even after the stress at 55° C. Prolonged treatments at 55° C. (48 hours, 72 hours and 96 hours) partially damage enzyme activity (FIG. 15, lanes 2, 3 and 4 respectively).

However, the lyophilized and ready-to-use mixtures containing 200 mM cellobiose have the same stability as mixtures containing 200 mM trehalose. We can therefore assert that, as a stabilizer, cellobiose has the same properties as trehalose, although, compared thereto, it has the aforenoted advantages which include its production by an enzyme hydrolysis system from cellulose, a molecule consisting of long glucose (sugar) chains of plant origin. The plant origin ensures the absence of possible nucleic acid contaminants originating from bacterial contaminations which is always likely when, as in the case of trehalose production, bacterial cultures are used to synthesize it.

Example 7

Use of the Cellobiose Stabilizer for Forming Ready-to-Use Compositions for Diagnostic Kits in the Parasitology Field Cellobiose was used as a stabilizer for the Hot Start DNA polymerase enzyme in the preparation of ready-to-use and lyophilized mixtures suitable for forming diagnostic kits in the parasitology field.

In particular for each of the investigated parasites, a final reaction mixture containing the following was prepared in advance:

10 mM Tris-HCl (pH 8.0), 50 mM KCl, 0.25 µM forward primer, 0.25 µM reverse primer, 0.2 mM dNTPs, 1.5 mM $MgCl_2$ and 2 Units of Taq Polymerase.

The triggers or primers for *Plasmodium* (one pair for each of the species *falciparum, malariae, vivax* and *ovale*) were designed in the conserved region of 18sRNA. The primers for *Leishmania* were designed in the conserved region of 18sRNA. The primers for *Toxoplasma* were designed in the highly repeating region HRE.

All the prepared mixtures contain an internal control corresponding to a primer pair designed in the human beta-globin gene sequences.

Each primer, in the various configurations, was supplied at concentrations of 0.25 µM.

Example 8

Comparison of the DNA Amplification and Direct Sequencing Performance

Agarose gel electrophoretic pattern of the wildtype (wt) DNA control sample (C1), a unknown DNA sample (C2), the mutant DNA control sample (C3) and the no template control (N) amplified.

DNA amplification was performed to compare the PCR products obtained with lyophilized and ready-to-use amplification mixtures and those obtained with a reference method.

To the lyophilized and ready-to-use amplification composition the following components were added:

| | |
|---|---|
| Primer Forward | 0.4 µM |
| Primer Reverse | 0.4 µM |
| DNA | 30 ng |
| H$_2$O | to 25 µl |

The reference method had the following composition:

| | |
|---|---|
| dNTPs | 0.2 mM each |
| Buffer reaction | 1x |
| MgCl$_2$ | 1.5 mM |
| Primer Forward | 0.4 µM |
| Primer Reverse | 0.4 µM |
| Taq polymerase | 0.003 U/µl |
| DNA | 30 ng |
| H$_2$O | to 25 µl |

PCR yield was comparable with both systems. Amplified products were analyzed by electrophoresis on a 2% agarose gel (FIG. 16a).

Before sequencing analysis, each PCR product was purified using MultiScreen HTS Vacuum Manifold system (Millipore). The purification procedure was performed in a shorter time for PCR products obtained using the Universal Master Mix compared with the ones obtained with the reference method. The freeze-dried form guaranteed high quality of PCR products, eliminating the presence of conventional additive that could disturb and delay the purification step, generating sufficient amounts of amplified products for subsequent sequencing analysis (FIG. 16b).

The results show that the lyophilized and ready-to-use amplification mixture (Universal Master Mix) is ideal for amplification reaction and subsequent sequencing analysis (FIG. 17).

Example 9

Comparison of Real Time PCR in Presence of a Fluorescent Dye, Melting Curve Analysis and High Resolution Melting Analysis (HRM) Performance The performance of the lyophilized and ready-to-use amplification mixture (Universal Master Mix) was evaluated by the use of Rotor Gene 6000 (Corbett Life Science). This instrument allowed 3 different applications in the same analytical session: a real time PCR in presence of a double strand specific dye (EvaGreen, Biotium), a Melting Curve analysis and a High Resolution Melting analysis. For each application the lyophilized and ready-to-use amplification mixture (Universal Master Mix) was compared to the reference method. For each of the 3 applications results are shown for a wildtype DNA control sample (C1), an unknown DNA sample (C2), a mutant DNA sample carrying an A>G substitution (C3), and a no template control (N).

showed a similar amplification efficiency

The results of the amplification analysis and the Real Time PCR take off values show that the lyophilized and ready-to-use amplification mixture (Universal Master Mix) is ideal for PCR and for Real Time PCR.

Melting analysis allowed the identification of a well defined melting temperature (T melting) both when using the lyophilized and ready-to-use amplification mixture (Universal Master Mix) and the reference method. In particular, the T melting of the samples obtained with the lyophilized and ready-to-use amplification mixture (Universal Master Mix) was identified at 89° C. while the one obtained with the reference method was identified at 87° C. Moreover, melting profiles obtained with the lyophilized and ready-to-use amplification mixture (Universal Master Mix) allowed a complete overlapping between the different samples; this condition is wasn't observed for the melting profiles obtained with the reference method.

The results of the Melting Curve analysis and of the High Resolution Melting analysis show that the lyophilized and ready-to-use amplification mixture (Universal Master Mix) is ideal for use in both applications.

Example 10

Comparison of the Performance in Quantitative Fluorescent (QF) PCR

The performance and the results obtained with the lyophilized and ready-to-use amplification mixture (Universal Master Mix) were evaluated and compared to those obtained with the reference method in QF PCR, in particular for prenatal diagnosis of the most common autosomal and sex chromosome aneuploidies. QF PCR analysis includes amplification, detection and analysis of chromosome-specific DNA microsatellites. Fluorescently labeled marker specific primers are used for PCR amplification of individual markers and the copy number of each marker is indicative of the copy number of the chromosome. The resulting PCR products may be analyzed and quantified using an automated genetic analyzer.

QF PCR Protocols:

| | |
|---|---|
| Reference method amplification mix | 7.5 µl |
| Primers set | 7.5 µl |
| DNA | 50 ng |
| H$_2$O | to 25 µl |

Composition

| | |
|---|---|
| Primers set | 7.5 µl |
| DNA | 50 ng |
| H$_2$O | to 25 µl |

QF PCR products were analyzed using the software GeneeMarker. The analysis of peak height and peak area ratios of each of the amplified products show that the lyophilized and ready-to-use amplification mixture (Universal Master Mix) is ideal is for use in Quantitative Fluorescence.

The invention claimed is:

1. An exsiccated or lyophilized composition comprising:
   a DNA polymerase enzyme, stabilized to withstand lyophilization and storage at a temperature up to 55° C., in a concentration in the range of 0.01 to 250 Units,
   cellobiose in a concentration in the range of 50 mM (17.115 g/L) to 500 mM (171.150 g/L) as the only carbohydrate and the only stabilizer, and
   a buffer.

2. The composition according to claim 1 wherein said DNA polymerase is selected from the group consisting of: Taq Polymerase, Hot Start Polymerase, and active fragments thereof.

3. The composition according to claim 1 or 2, comprising 250 mM cellobiose and 2 Units of DNA polymerase enzyme.

4. A process for the amplification of nucleic acids comprising the steps of:
   reconstituting the composition according to claim 1 in water or in a buffer;
   adding primers specific for a target DNA;
   adding a nucleic acid template; and
   adding one or more of the reagents selected from the group consisting of: KCl, MgCl$_2$, dNTPs, at least one optionally labelled probe, reducing agents and further stabilizers; further wherein said amplification comprises the steps of:
   (i) denaturing a template DNA;
   (ii) annealing at least one primer to a complementary strand of said template DNA; and
   (iii) elongating said primer by use of the DNA polymerase enzyme of the composition according to claim 1 or an active fragment thereof.

5. A composition comprising:
   a DNA polymerase enzyme stabilized to withstand lyophilization and storage at a temperature up to 55° C., in a concentration in the range of 0.01 to 250 Units,
   cellobiose in a concentration in the range of 50 mM to 500 mM as the only carbohydrate and the only stabilizer, and
   a buffer, dNTPs, KCl and MgCl$_2$.

6. The composition according to claim 1 or 5, wherein said buffer is Tris HCl.

7. The composition according to claim 5 further comprising one or more further components selected from the group consisting of reducing agents and at least one probe, which is optionally labeled; further wherein the reducing agents are selected from the group consisting of: β-mercaptoethanol and DTT.

8. A method for the amplification of nucleic acids by using the composition according to claim 1 or 5, the method comprising the steps of:
   (i) denaturing a template DNA;
   (ii) annealing at least one primer to a complementary strand of said template DNA; and
   (iii) elongating said primer by use of the DNA polymerase enzyme of the composition according to claim 1 or 5 or an active fragment thereof.

9. A method for the amplification of nucleic acids by using the composition according to claim 1 or 5, wherein said amplification process is carried out in an automated fashion and comprises the steps of:
   (i) denaturing a template DNA;
   (ii) annealing at least one primer to a complementary strand of said template DNA; and
   (iii) elongating said primer by use of the DNA polymerase enzyme of the composition according to claim 1 or 5 or an active fragment thereof.

10. A method for the amplification of nucleic acids by using the composition according to claim 1 or 5, wherein said amplification of nucleic acids is by PCR, Real Time PCR, Sequencing, Quantitative Fluorescent PCR, Multiplex PCR, Whole Genome Amplification or Isothermal Amplification, the method comprising the steps of:
   (i) denaturing a template DNA;
   (ii) annealing at least one primer to a complementary strand of said template DNA; and
   (iii) elongating said primer by use of the DNA polymerase enzyme of the composition according to claim 1 or 5 or an active fragment thereof.

11. A process for the amplification of nucleic acids comprising the steps of:
reconstituting the composition according to claim 5 in lyophilized form in water or in a buffer;
adding primers specific for a target DNA;
adding a nucleic acid template;
optionally adding at least one optionally labelled probe, reducing agents and further stabilizers, further wherein said amplification comprises the steps of:
(i) denaturing a template DNA;
(ii) annealing at least one primer to a complementary strand of said template DNA; and
(iii) elongating said primer by use of the DNA polymerase enzyme of the composition according to claim 1 or an active fragment thereof.

12. A ready-to-use product comprising:
the composition of claim 1 or 5 in exsiccated or lyophilized form;
a solvent for reconstituting said composition.

13. A kit for PCR amplification of a DNA sample comprising the composition according to claim 1 or 5 and optionally instructions for the reconstitution and use of the enzyme in a polymerase chain reaction.

14. A method for preparing a stabilized composition comprising a nucleic acid polymerase, the method comprising lyophilizing or exsiccating a composition comprising said nucleic acid polymerase and cellobiose, wherein cellobiose is used in said method as the sole carbohydrate and the sole stabilizer.

15. A method for preserving and storing a nucleic acid polymerase in a stabilized form, the method comprising lyophilizing or exsiccating said nucleic acid polymerase in the presence of cellobiose, wherein said nucleic acid polymerase is a DNA polymerase, and wherein cellobiose is used in said method as the sole carbohydrate and the sole stabilizer.

* * * * *

SEQUENCE LISTING

```
<160> NUMBER OF SEQ ID NOS: 2

<210> SEQ ID NO 1
<211> LENGTH: 14
<212> TYPE: DNA
<213> ORGANISM: Unknown
<220> FEATURE:
<223> OTHER INFORMATION: Wildtype sequence amplified product of unknown
      organism

<400> SEQUENCE: 1
ttgcttcaac agtg                                                       14

<210> SEQ ID NO 2
<211> LENGTH: 14
<212> TYPE: DNA
<213> ORGANISM: Unknown
<220> FEATURE:
<223> OTHER INFORMATION: mutant sequence amplified product of unknown
      organism

<400> SEQUENCE: 2
ttgcttcgac agtg                                                       14
```